(12) United States Patent
Clemmer et al.

(10) Patent No.: US 11,420,205 B2
(45) Date of Patent: Aug. 23, 2022

(54) INSTRUMENT AND METHOD FOR ENERGIZING MOLECULES IN CHARGED DROPLETS

(71) Applicants: INDIANA UNIVERSITY RESEARCH AND TECHNOLOGY CORPORATION, Indianapolis, IN (US); THE TEXAS A&M UNIVERSITY SYSTEM, College Station, TX (US)

(72) Inventors: David E. Clemmer, Bloomington, IN (US); Tarik J. El-Baba, Bloomington, IN (US); Daniel R. Fuller, Bloomington, IN (US); Daniel W. Woodall, Bloomington, IN (US); David H. Russell, Bryan, TX (US); Evan R. Williams, Oakland, CA (US)

(73) Assignees: Indiana University Research and Technology Corp., Indianapolis, IN (US); The Texas A&M University System, College Station, TX (US)

(*) Notice: Subject to any disclaimer, the term of this patent is extended or adjusted under 35 U.S.C. 154(b) by 197 days.

(21) Appl. No.: 16/772,394

(22) PCT Filed: Dec. 5, 2018

(86) PCT No.: PCT/US2018/064005
§ 371 (c)(1),
(2) Date: Jun. 12, 2020

(87) PCT Pub. No.: WO2019/118242
PCT Pub. Date: Jun. 20, 2019

(65) Prior Publication Data
US 2021/0078004 A1 Mar. 18, 2021

Related U.S. Application Data

(60) Provisional application No. 62/599,371, filed on Dec. 15, 2017.

(51) Int. Cl.
*B01L 3/00* (2006.01)
*G01N 33/68* (2006.01)
*H01J 49/16* (2006.01)

(52) U.S. Cl.
CPC .... *B01L 3/502784* (2013.01); *G01N 33/6851* (2013.01); *B01L 2300/1866* (2013.01); *B01L 2400/02* (2013.01)

(58) Field of Classification Search
CPC .............................. H01J 49/165; H01J 49/167
See application file for complete search history.

(56) References Cited

U.S. PATENT DOCUMENTS 7,772,548 B2* 8/2010 Wollnik ................ H01J 49/145
250/288
8,766,179 B2 7/2014 Kaltashov et al.

OTHER PUBLICATIONS

Anderson, Jens Ulrik et al. "The combination of an electrospray ion source and an electrostatic storage ring for lifetime and spectroscopy experiments on biomolecules." Review of Scientific Instruments (2002) 73 1284. (Year: 2002).*

(Continued)

*Primary Examiner* — Christopher Adam Hixson
(74) *Attorney, Agent, or Firm* — Barnes & Thornburg LLP

(57) ABSTRACT

An instrument for energizing molecules contained in a sample solution may include a droplet generator configured to generate droplets of the sample solution. The droplet generator illustratively has an elongated nozzle defining an orifice at one end thereof from which the droplets exit the droplet generator, and the orifice illustratively defines a first longitudinal axis centrally therethrough. A molecule energizing source is configured to produce a molecule energizing field, and is positioned relative to the nozzle orifice such that the molecule energizing field extends into at least some of the generated droplets along a direction non-parallel with the (Continued)

first longitudinal axis. The molecule energizing field illustratively carries energy which heats at least one of the generated droplets sufficiently to induce structural changes in at least one molecule contained in the at least one of the generated droplets.

30 Claims, 12 Drawing Sheets

(56) References Cited

OTHER PUBLICATIONS

Ninomiya, Satoshi et al. "Vacuum electrospray of volatile liquids assisted by infrared laser irradiation." Rapid Communication in Mass Spectrometry (2012) 26 863-869. (Year: 2012).*
El-Baba et al., "Melting proteins in charged droplets using 10.6um light", Department of Chemistry, Indiana University, no date given, 5 pages.
El-Baba et al., "Evidence for Trapped Intermediates upon Melting Single Protein molecules Confined in Droplets with 10.6um light", Department of Chemistry, Indiana University, no date given, 6 pages.
El-Baba et al., "Melting Proteins: Evidence for Multiple Stable Structures upon Thermal Denaturation of Native Ubiquitin from Ion Mobility Spectrometry-Mass Spectrometry Measurements", Journal of the American Chemical Society, published Apr. 20, 2017, pp. 6306-6309.
El-Baba et al., "Melting proteins confined in nanodroplets with 10.6 um light provides clues about early steps of denaturation", Royal Society of Chemistry, Chem. Commun., 2018, 54, 3270.
Hiraoka et al., "High-sensitivity negative-ion laser spray for liquid chromatography/mass spectrometry", Rapid Communications in Mass Spectrometry, 2001; 15: 2020-2026.
Hiraoka et al., "A New Liquid Chromatography/Mass Spectrometry Interface: Laser Spray", Rapid Communications in Mass Spectrometry, 12, 1170-1174 (1998).
Kudaka et al., "A comparative study of laser spray and electrospray" Rapid Communications in Mass Spectrometry, 14, 1558-1562 (2000).
Lee, Jae Kyoo, et al. "Microdroplet fusion mass spectrometry for fast reaction kinetics", PNAS, Mar. 31, 2015, vol. 112, No. 13, pp. 3898-3903.
Nakamura et al., "Denaturation of a-lactalbumin and ubiquitin studied by electrospray and laser spray", Rapid Communications in Mass Spectrometry, 2007; 21:1635-1643.
Shi et al., "Thermal unfolding of proteins probed by laser spray mass spectrometry", Rapid Communications in Mass Spectrometry, 2008; 22: 1430-1436.
Takamizawa et al., "Denaturation of Lysozyme and Myoglobin in Laser Spray", American Soxiety for Mass Spectrometry, 2005, 16, 860-868.
Takamizawa et al., "Measurement of sugars using the laser spray technique with a gold capillary", Rapid Communications in Mass Spectrometry, 2008; 22:2453-2456.
PCT International Search Report and Written Opinion completed by the ISA/EP dated Feb. 17, 2019 and issued in connection with PCT/US2018/064005.
Tarick J. El-Baba et al, "Melting Proteins: Evidence for Multiple Stable Structures upon Thermal Denaturation of Native Ubiquitin from Ion Mobility Spectrometry-Mass Spectrometry Measurements", Journal of the American Chemical Society, vol. 139, No. 18, Apr. 26, 2017 (Apr. 26, 2017), p. 6306-6309.
Tarick J. El-Baba et al, "Melting proteins confined in nanodroplets with 10.6 [mu]m light provides clues about early steps of denaturation", Chemical Communications, vol. 54, No. 26, Mar. 8, 2018 (Mar. 8, 2018), p. 3270-3273.
Samuel I. Merenbloom et al, "IMS-IMS and IMS-IMS-IMS/MS for Separating Peptide and Protein Fragment Ions", Analytical Chemistry, vol. 78, No. 8, Apr. 1, 2006 (Apr. 1, 2006), p. 2802-2809.
Xiao Cong et al, "Determining Membrane Protein-Lipid Binding Thermodynamics Using Native Mass Spectrometry", Journal of the American Chemical Society, vol. 138, No. 13, Mar. 25, 2016 (Mar. 25, 2016), p. 4346-4349.
Guanbo Wang et al, "Direct Monitoring of Heat-Stressed Biopolymers with Temperature-Controlled Electrospray Ionization Mass Spectrometry", Analytical Chemistry, vol. 83, No. 8, Apr. 15, 2011 (Apr. 15, 2011), p. 2870-2876.
Justin L. P. Benesch et al, "Thermal Dissociation of Multimeric Protein Complexes by Using Nanoelectrospray Mass Spectrometry", Analytical Chemistry, vol. 75, No. 10, May 1, 2003 (May 1, 2003), p. 2208-2214.

* cited by examiner

INSTRUMENT AND METHOD FOR ENERGIZING MOLECULES IN CHARGED DROPLETS

CROSS-REFERENCE TO RELATED APPLICATION

This application is a U.S. national stage entry of PCT Application No. PCT/US2018/064005, filed Dec. 5, 2018, which claims priority to, and the benefit of, U.S. Provisional Patent Application No. 62/599,371, filed Dec. 15, 2017, the disclosures of which are expressly incorporated herein by reference in their entireties.

GOVERNMENT RIGHTS

This invention was made with government support under GM117207 and GM121751 awarded by the National Institutes of Health. The Government has certain rights in the invention.

FIELD OF THE INVENTION

The present invention relates generally to instruments and methods for energizing molecules in charged droplets, and more specifically to instruments and methods for energizing such molecules by irradiating or otherwise heating the charged droplets, and/or by otherwise producing energized charged droplets.

BACKGROUND

The stability of a protein is a fundamental property that is influenced by numerous factors, including the protein's environment (e.g., solution pH, buffer type, cosolvent fractions, excipients, and environmental impurities), amino acid sequence purity and degradation (e.g., to what extent have processes such as deamidation of acidic sidechains taken place), the numbers, types, and positions of post-translational modifications, the binding of ligands, as well as the fidelity of the folded state (e.g., are helices, sheets, and turns, as well as the cis- and trans-peptide bonds of proline configured properly). Because of this, a protein's melting temperature ($T_m$, the point where the fractions of folded and unfolded states are equal (such that the Gibb's free energy of the system, $\Delta G=0$)) is a benchmarking biophysical property which provides insight about the fidelity and potency of the folded-state in a defined environment.

The determination of reproducible melting temperatures conventionally requires large quantities (μg-mg) of protein as purified sequences having known modifications, reproducibly folded in well-characterized environments. Moreover, once samples are available, a single melting curve measurement using conventional techniques may require, for example, up to an hour to record. Heretofore, melting curve determinations have thus been arduous, and it is therefore desirable to develop instruments and/or techniques which reduce the time and/or complexity associated with conducting melting curve analyses.

SUMMARY

The present invention may comprise one or more of the features recited in the attached claims, and/or one or more of the following features and combinations thereof. In one aspect, an instrument for energizing molecules contained in a sample solution may comprise a droplet generator configured to generate droplets of the sample solution, and a molecule energizing source. The droplet generator illustratively has an elongated nozzle defining an orifice at one end thereof from which the droplets exit the droplet generator, and the orifice illustratively defines a first longitudinal axis centrally therethrough. The molecule energizing source is configured to produce a molecule energizing field, and is illustratively positioned relative to the nozzle orifice such that the molecule energizing field extends into at least some of the generated droplets along a direction non-parallel with the first longitudinal axis. The molecule energizing field illustratively carries energy which heats at least one of the generated droplets sufficiently to induce structural changes in at least one molecule contained in the at least one of the generated droplets.

In another aspect, an instrument for energizing molecules contained in a sample solution may comprise a droplet generator configured to generate droplets of the sample solution, the droplet generator having an elongated nozzle defining an orifice at one end thereof from which the droplets exit the droplet generator, the orifice defining a first longitudinal axis centrally therethrough, and a molecule energizing source configured to produce energy and positioned relative to the nozzle orifice such that the produced energy is applied to at least one of the generated droplets exiting the droplet generator, the produced energy inducing at least one structural change in at least one molecule contained in the at least one of the generated droplets. Examples of such a molecule energizing source may be or include, but should not be limited to, one or any combination of at least one laser configured to produce at least one molecule energizing field carrying the produced energy and extending into at least some of the generated droplets along a direction non-parallel with the first longitudinal axis such that the produced energy carried by the molecule energizing field heats the at least one of the generated droplets sufficiently to induce the at least one structural change in the at least one molecule contained in the at least one of the generated droplets, at least one source of heated gas configured to produce the energy in the form of thermal energy contained in the heated gas which heats the at least one of the generated droplets sufficiently to induce the at least one structural change in the at least one molecule contained in the at least one of the generated droplets, a tube separate from the nozzle and defining a passageway through which the at least one of the generated droplets passes along with a heating source configured to heat the tube to produce the thermal energy within the passageway, and the like. In any of these examples, the produced energy may alternatively or additionally induce a chemical reaction within the at least one of the generated droplets, and the induced chemical reaction within the at least one of the generated droplets may result in the at least one structural change in at least one molecule contained in the at least one of the generated droplets.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1:
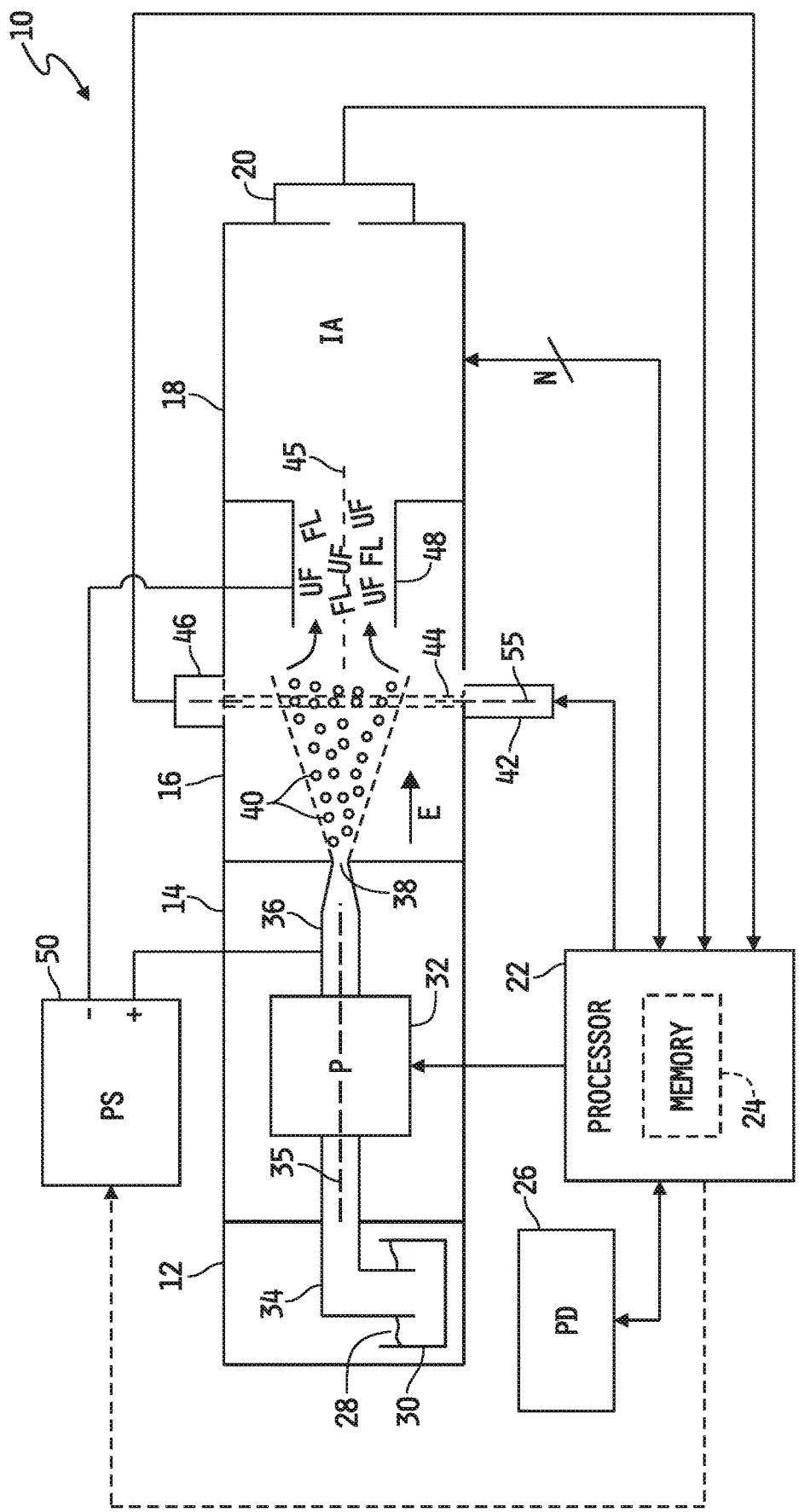
FIG. 1 is a block diagram of an embodiment of an instrument for energizing molecules in charged droplets and for analyzing one or properties of such energized molecules.

Referring to FIG. 1, a block diagram is shown of an embodiment of an instrument 10 for energizing molecules in charged droplets and for analyzing one or properties of such energized molecules. In the illustrated embodiment, the instrument 10 includes a sample source 12 coupled to a droplet generator 14. The droplet generator 14 is configured to produce droplets 40 containing one or more analytes from the sample source 12, and to provide such droplets to a molecule energizing stage 16 in which at least some of the droplets 40 are thermally excited and/or in which at least one chemical reaction is induced thermally or via electromagnetic radiation. The molecule energizing stage 16 is coupled to an inlet of an ion analyzer 18 having an outlet coupled to a conventional ion detector 20. One or more of the foregoing components of the instrument 10 may be controlled, at least in part, by a processor 22. In some embodiments, the processor 22 includes and/or is coupled to a memory unit 24. The processor 22 is illustratively coupled to one or more peripheral devices 26 for providing signal input to the processor 22 and/or to which the processor 22 provides signal output. In some embodiments, the memory 24 has instructions stored therein which, when executed by the processor 22, cause the processor 22 to control one or more of the droplet generator 14, the molecule energizing stage 16, the ion analyzer 18 and one or more output peripheral devices 26, and/or which cause the processor 22 to process input signals received from one or more of input peripheral devices 26.

The ion detector 20 is positioned to detect ions at an outlet of the ion analyzer 18, and is electrically connected to an input of the processor 22. Signals produced by the ion detector 20 in response to detection of ions are provided to the processor 22, and the processor 22 is operable to process the signals to produce ion spectral information for display or storage. The one or more peripheral devices 26 may include any number of conventional input devices, examples of which may include, but are not limited to, a keyboard, a point-and-click input device, a touch-screen or touch-pad input device, an input data port configured to receive input data from an external device or system and the like. The one or more peripheral devices 26 may alternatively or additionally include any number of conventional output devices, examples of which may include, but are not limited to, one or more display monitors, one or more memory units to store output data, one or more printing or plotting device, and the like.

In the example embodiment depicted in FIG. 1, the sample source 12 illustratively includes sample solution 28 disposed in a sample container 30. The sample solution 28 generally includes a sample containing one or more analytes dissolved in or carried by a solvent. In some embodiments, the sample may be a biological sample including, but not limited to, one or more proteins. Alternatively or additionally, the sample may be or include one or more non-biological components. The solvent may be or include any conventional solvent including, for example, but not limited to, water or a solution containing water. In one example embodiment, which should not be considered limiting in any way, the sample solution 28 is an aqueous solution containing one or more biological components such as one or more proteins or the like.

The droplet generator 14 may be any conventional droplet generator capable of generating droplets 40 of a suitable size from the sample solution 28. In some embodiments, the droplet generator 14 is configured to produce droplets 40 having diameters in the range of 0.005-1 µm, although in other embodiments the droplet generator 14 may be configured to produce droplets 40 of any size without limitation. In the embodiment illustrated in FIG. 1, the droplet generator 14 is illustratively provided in the form of a conventional electrospray ion (ESI) source including a pump 32 having an inlet coupled to one end of an inlet tube or capillary 34 and an outlet coupled to one end of an outlet capillary or nozzle 36. The opposite end of the inlet tube or capillary 34 is inserted into the sample container 30 in fluid communication with the sample solution 28, and the opposite end of the outlet capillary or nozzle 36 defines an outlet orifice 38 of the ESI source 14. In some alternate embodiments, the pump 32 may be omitted.

In embodiments which include the pump 32, its operation is conventional, and in some such embodiments operation of the pump 32 may be controlled by the processor 22 in a conventional manner. In embodiments which include it, the pump 32, is generally operable to draw the sample solution 28 from the sample container 30 and to force the sample solution 28 from the outlet orifice 38 of the nozzle 36 in the form of an expelled spray or mist. The size of the droplets 40 forming the spray or mist is generally a function of the diameter of the outlet orifice 38 of the nozzle 36. In embodiments which do not include the pump 32, the droplets 40 may be formed by energizing the nozzle 36 and the droplets 40 may exit the outlet orifice 38 of the nozzle 36 via capillary action. In any case, it is generally known that droplet diameters of approximately 1/20 of the diameter of an outlet orifice 38 of a conventional ESI source 14 can be achieved, and in order to produce droplets 40 having diameters in the range of 0.005-1 µm as described above requires the diameter of the outlet orifice 38 of the nozzle 36 to be in the range of 0.01-20 µm.

Generally, the number of sample components that may be contained within single droplets 40 is proportional to the size of the droplets 40. Of course, the type of sample will also have a bearing on the number of sample components that may be contained within single droplets 40 since the type of sample will generally dictate the size(s) of the sample components contained in the droplets 40. The droplet generator 14 may thus be configured, taking into account the type of sample(s) in the sample solution 28, to produce droplets 40 of any desired size to correspondingly control the number of sample components that will be contained within single droplets 40 produced by the droplet generator 14. As will be described in greater detail in the following set of examples, it is advantageous in some embodiments to configure the droplet generator 14 to produce droplets 40 having droplet diameters which restrict the number of sample components contained therein to one sample component per droplet 40. As one specific example, in embodiments in which the sample solution 28 contains proteins, it has been found that configuring the droplet generator 14 to produce droplets 40 having droplet diameters of approximately 0.01 µm is sufficient to restrict the number of proteins contained therein to one per droplet 40. In such embodiments, the diameter of the nozzle orifice 38 is accordingly sized to be approximately 0.2 µm. Droplets 40 having diameters larger than approximately 0.01 µm will, in this specific example, allow for two or more proteins per droplet 40.

In some embodiments, as illustrated by example in FIG. 1, the droplets 40 emitted or expelled from the droplet generator 14 are made to move toward an ion inlet 48, e.g., an inlet capillary, tube, opening, orifice or the like, of the ion analyzer 18 by establishing a suitably oriented electric field, E, between the nozzle orifice 38 and the ion inlet 48. In some such embodiments, both the nozzle 36 and the ion inlet 48 of the ion analyzer 18 are formed of one or more electrically conductive materials, and a conventional power source 50, e.g., a DC power source, is operatively connected between them. In the illustrated embodiment, the positive output of the DC power source 50 is connected to the nozzle 36 and the negative or ground output of the DC power source 50 is connected to the ion inlet 48 of the ion analyzer 18 such that an electric field, E, is established in the direction depicted in FIG. 1 which will draw positively charged particles toward the ion inlet 48. In other embodiments, the polarities of the power source 50 may be reversed to establish an oppositely-directed electric field which will draw negatively charges particles toward the ion inlet 48. In either case, as illustrated by dashed-line configuration in FIG. 1, the nozzle 36 of the droplet generator 14 defines a longitudinal axis 35 centrally therethrough which is illustratively collinear with a longitudinal axis 45 defined centrally through the ion inlet 48 of the ion analyzer 18 so that droplets 40 exiting the nozzle orifice 38 are directed by the electric field, E, into the ion inlet 48 of the ion analyzer 18. In alternate embodiments, the longitudinal axis 35 of the nozzle 36 need not be collinear with the longitudinal axis 45 defined centrally through the ion inlet 48.

The molecule energizing stage 16 illustratively includes a molecule energizing source 42 configured to create a molecule energizing area or field 44 through which the droplets 40 pass under the influence of the electric field E. In some embodiments, the molecule energizing source 42 is controllable by the processor 22 to control one or more properties of the molecule energizing field 44, examples of which may include, but are not limited to, the power of the molecule energizing field 44, the duration(s) of the molecule energizing field 44 and the direction of the molecule energizing field 44. Although not depicted separately from the molecule energizing source 42 in FIG. 1, a suitable source of energy, e.g., such as one or more conventional sources of electrical power, will typically supply working or operating energy to the molecule energizing source 42. In some embodiments, for example, the electrical power source 50 may provide, or may be configured to provide, such working or operating energy to the molecule energizing source 42 in the form of electrical power. In other embodiments, one or more other conventional sources of electrical and/or other energy may be operatively coupled to the molecule energizing source 42.

In one embodiment, as illustrated in FIG. 1, the molecule energizing source 42 is provided in the form of a conventional laser configured to produce a molecule energizing field 44 in the form of collimated electromagnetic radiation. In such embodiments, the processor 22 may be configured to control one or more of the power of the radiation field 44, the duration(s) of application of the radiation field 44, the direction of the radiation field 44 and the wavelength of the radiation field 44. Further in such embodiments, a conventional power meter 46 may be positioned opposite to the radiation output of the laser 42 and electrically connected to the processor 22 so that the processor can monitor the output power of the laser 42, and to use the output power measurements to control the output of the laser 42 in a conventional manner. In other embodiments, the power meter 46 may be omitted.

In the illustrated embodiment, the laser 42 is positioned relative to the molecule energizing stage 16 such that a longitudinal axis 55 defined centrally through the collimated radiation field 44 produced by the laser 42 is approximately orthogonal to the collinear longitudinal axes 35, 45 of the droplet generator 14 and ion analyzer 18 respectively, and is thus approximately orthogonal to the direction of the electric field, E, and therefore the direction of travel of the droplets 40. In other embodiments, the laser 42 may be alternately positioned relative to the molecule energizing stage 16 such that the longitudinal axis 55 of the radiation field 44 produced by the laser 42 forms a non-orthogonal angle with respect to the collinear longitudinal axes 35, 45. The angle may be any angle greater (or less) than zero such that the radiation field 44 is not parallel with the collinear axes 35, 45.

Figure 3A:
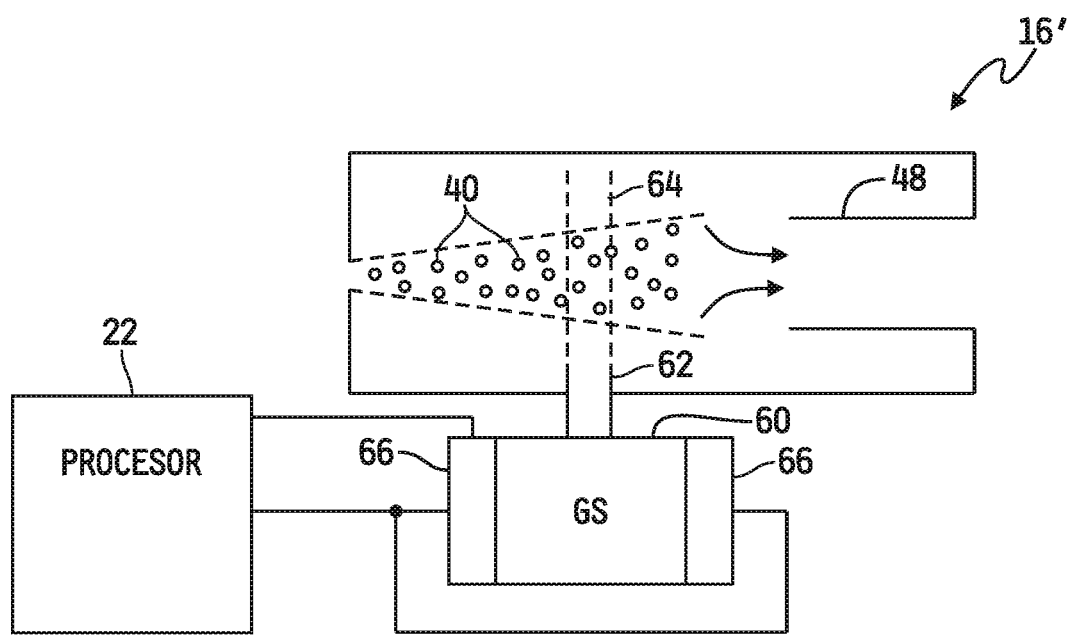
FIG. 3A is a block diagram of another embodiment of the molecule energizing source of the instrument illustrated in FIG. 2.
Figure 3B:
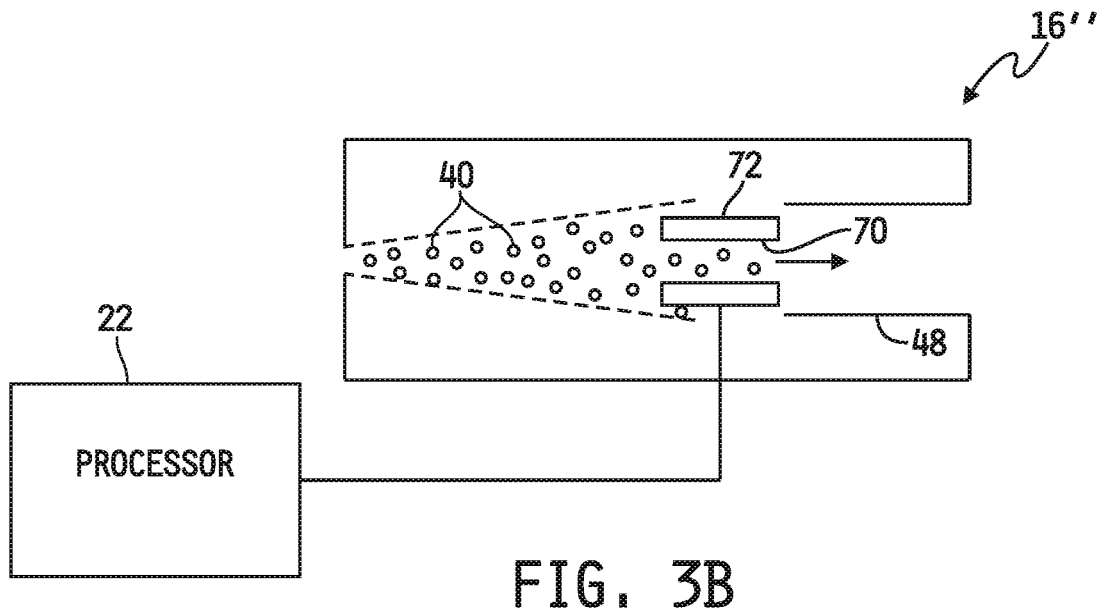
FIG. 3B is a block diagram of yet another embodiment of the molecule energizing source of the instrument illustrated in FIG. 2.
Figure 3C:
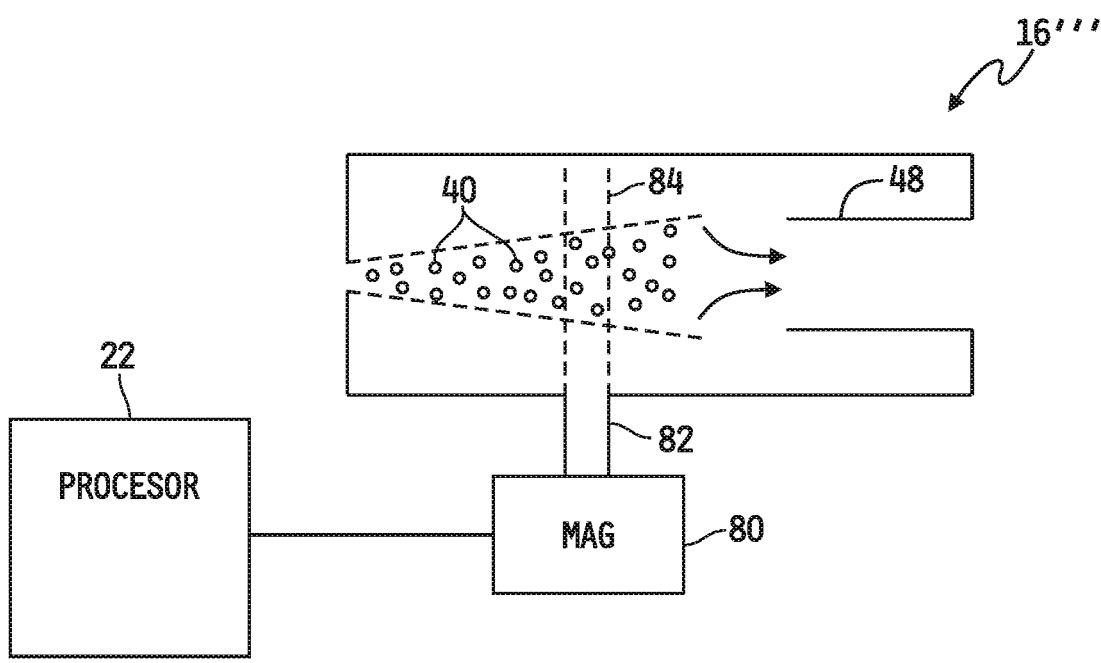
FIG. 3C is a block diagram of still another embodiment of the molecule energizing source of the instrument illustrated in FIG. 2.

In some embodiments, the molecule energizing source 42 may include two or more lasers each positioned relative to the molecule energizing stage 16 to direct a collimated radiation field into the droplets 40 produced by the droplet generator 14 prior to entry into the ion analyzer 18. In some such embodiments at least two such lasers may be positioned such that the collimated radiation fields produced thereby are parallel with each other. In other embodiments, the molecule energizing source 42 may include one or more other sources of energy in place of or in addition to one or more lasers, some non-limiting examples of which are illustrated in FIGS. 3A-3C. In any case, the one or more molecule energizing sources 42 is/are illustratively operable to transfer energy to one or more of the droplets 40 in a form which heats at least one of the generated droplets 40 sufficiently to induce structural changes in at least one molecule contained therein.

In one specific implementation in which the sample components are proteins, the one or more molecule energizing sources 42 is/are illustratively operable to transfer energy to one or more of the droplets 40 to heat at least one of the generated droplets 40 sufficiently to cause at least one previously folded protein in at the least one of the generated droplets 40 to unfold or to at least begin to unfold. The one or more molecule energizing sources 42 in this example may be or include a 10.6 μm $CO_2$ laser configured or controllable to produce a collimated radiation field of up to at least 50 Watts or more. In some such embodiments, the processor 22 may be programmed to control the output power of the laser 42, e.g., in a conventional open-loop configuration or in a conventional feedback configuration using laser power measurements provided by the power meter 46 in embodiments which include it. Alternatively or additionally, the output power of the laser 42 may be controlled manually. In embodiments in which the droplet generator 14 is configured to produce droplets 40 with a diameter sized such that each droplet 40 contains a single protein, the radiation field 44 will be configured to cause at least some proteins to partially or fully unfold such that some proteins entering the ion inlet 48 of the ion analyzer 18 are unfolded (depicted as "UF" in FIG. 1) and some remain folded (depicted as "FL" in FIG. 1). Although not specifically depicted in FIG. 1, others of the droplets 40 entering the ion inlet 48 of the ion analyzer 18 may be partially unfolded (or partially folded), wherein the term "partially folded" or "partially unfolded" are synonymous and should be understood to mean any of potentially multiple unfolding states through which the protein(s) may advance as the protein(s) transition, under the influence of the radiation field 44, from a folded state to a fully unfolded state. In such embodiments, the molecule energizing source 42 is illustratively selected and/or controlled to produce a molecule energizing field with sufficient intensity to cause the proteins to undergo "melting"-like transitions within the droplet 40 prior to solvent evaporation and ion formation, as will be described in greater detail in the following examples.

The ion analyzer 18 may be or include one or more conventional instruments configured to measure one or more molecular properties. Examples may include, but are not limited to, a mass analyzer, a mass spectrometer, an ion mobility spectrometer, a gas chromatograph and the like. In some embodiments, the ion analyzer 18 may include one or more similar and/or different instruments disposed in a cascaded arrangement. In some embodiments, the ion analyzer 18 may alternatively or additionally include one or more additional molecular processing stages such as, but not limited to, one or more ion traps, one or more ion fragmentation (dissociation) chambers or regions and the like. As one specific example, the ion analyzer 18 may take the form of a single mass spectrometer (MS) or a cascaded arrangement of two or more mass spectrometers, e.g., MS-MS. As another specific example, the ion analyzer 18 may take the form of a single ion mobility spectrometer (IMS) or a cascaded arrangement of two or more ion mobility spectrometers, e.g., IMS-IMS. As yet another specific example, the ion analyzer 18 may take the form of one (IMS) or a cascaded arrangement of two or more ion mobility spectrometers, e.g., IMS-IMS, followed by one (MS) or a cascaded arrangement of two or more mass spectrometers, e.g., MS-MS, or vice versa. In any of the foregoing embodiments one or more ion traps and/or one or more ion dissociation chambers or regions may be interposed prior to, following or in between one or more of the above-described instruments or stages.

Figure 2:
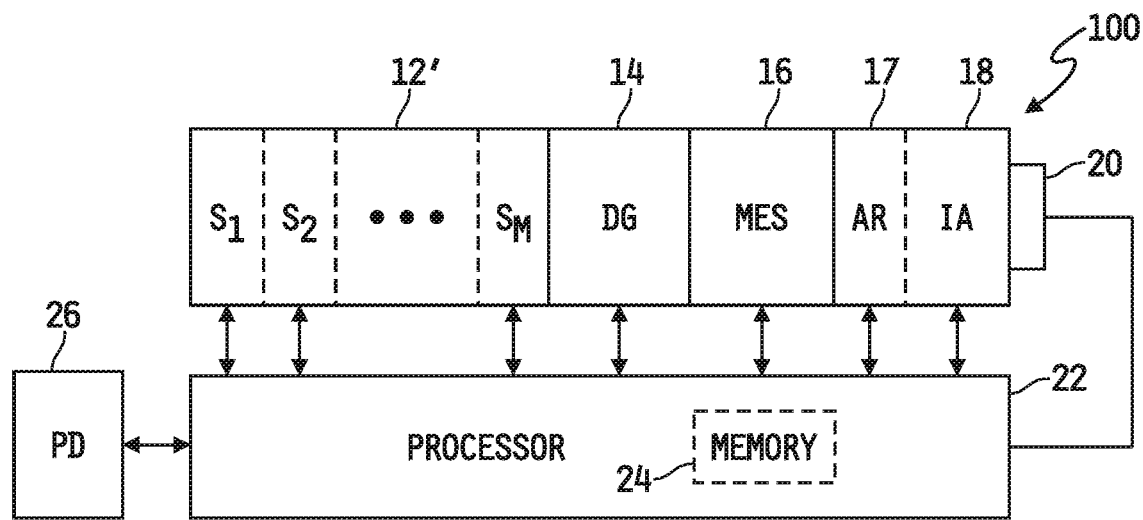
FIG. 2 is a block diagram of another embodiment of an instrument for energizing molecules in charged droplets and for analyzing one or properties of such energized molecules.

Referring now to FIG. 2, anther embodiment is shown of an instrument 100 for energizing molecules in charged droplets and for analyzing one or properties of such energized molecules. The instrument 100 is identical in many respects to the instrument 10 illustrated in FIG. 1 and described above, and components in common with the instrument 10 are labeled in FIG. 2 with identical labels. For brevity, such components will not be described again here, and it will be understood that the structure(s) and operation of such components are as described with respect to FIG. 1. The instrument 100 differs from the instrument 10 primarily in the structure and operation of the sample source 12'. As depicted in FIG. 2, the sample source 12' may illustratively include any number, M, of cascaded stages $S_1$-$S_M$, where M may be any integer greater than 1. In all embodiments of the sample source 12', the sample source stage $S_1$ contains the sample to be analyzed/measured.

In some embodiments, the sample source stage $S_1$ may include a sample solution 28 disposed in a sample container 30 as illustrated in FIG. 1, and in other embodiments the sample source stage $S_1$ may contain a solid or other non-solution sample. In some embodiments, the sample source stage $S_2$ contains a sample ionization stage. In such embodiments, the sample ionization stage $S_2$ may contain any conventional ionization structure or assembly, examples of which may include, but are not limited to, an electrospray ionization (ESI) unit, a matrix-assisted laser desorption/ionization (MALDI) unit or the like. In some such embodiments, the sample source stage $S_2$ may include a solvation stage. In any case, in embodiments which include such a sample source stage $S_2$, the remaining stages $S_3$-$S_{M-1}$ may include any combination of one or more instruments configured to separate ions in time according to one or more molecular characteristics, one or more ion selection and/or storage chambers, e.g., one or more ion traps and/or one or more ion dissociation chambers, stages or regions. As one example, the stages $S_3$-$S_{M-1}$ may include one or more ion separation instruments. In embodiments which include a single ion separation instrument, the instrument may be any conventional instrument configured to separate ions in time according to a specified molecular characteristic. Examples of such an ion separation instrument may include, but are not limited to, a gas chromatograph, a mass analyzer, a mass spectrometer (MS) and an ion mobility spectrometer (IMS). In embodiments which include two or more ion separation instruments, such instruments are illustratively arranged in cascaded stages. In some such embodiments, any two adjacent stages may operate to separate ions according to the same or a different molecular characteristic. Example cascaded arrangements of ion separation instruments may include, but are not limited to, IMS-MS, IMS-IMS, MS-MS, IMS-IMS-MS-MS and the like.

As another example, the stages $S_3$-$S_{M-1}$ may include one or more ion separation instruments, as just described, followed by an ion trap configured to collect and store ions generally and/or to collect and store only ions having a selected molecular characteristic or a selected range of molecular characteristics, e.g., a selected ion mobility, a selected range of ion mobilities, a selected ion mass-to-charge ratios, a selected range of ion mass-to-charge ratios, etc.

As yet another example, the stages $S_3$-$S_{M-1}$ may include a dissociation stage, region or chamber followed by one or more ion separation instruments, as just described. In such embodiments, the dissociation stage or chamber may be conventional and configured in a known manner to dissociate or fragment parent ions into daughter ions. Dissociation or fragmentation of ions in the dissociation stage or chamber may be carried out in any conventional manner, examples of which include, but are not limited to, collision-induced dissociation (CID), surface-induced dissociation (SID), electron transfer dissociation (ETD), electron capture dissociation (ECD), photo-induced dissociation (PID) and any combination thereof. In such embodiments, the one or more ion separation instruments may be followed by an ion trap configured to collect and store ions generally and/or to collect and store only ions having a selected molecular characteristic or a selected range of molecular characteristics.

As a further example, the stages $S_3$-$S_{M-1}$ may include one or more ion separation instruments, as just described, followed by a dissociation or fragmentation stage, region or chamber followed by an ion trap configured to collect and store ions generally and/or to collect and store only ions having a selected molecular characteristic or a selected range of molecular characteristics.

As still a further example, the stages $S_3$-$S_{M-1}$ may include a dissociation or fragmentation stage, region or chamber followed by an ion trap configured to collect and store ions generally and/or to collect and store only ions having a selected molecular characteristic or a selected range of molecular characteristics.

In yet a further example, the stages $S_3$-$S_{M-1}$ may include a first dissociation or fragmentation stage, region or chamber followed by one or more ion separation instruments, as just described, followed by a second dissociation or fragmentation stage, region or chamber, followed by an ion trap configured to collect and store ions generally and/or to collect and store only ions having a selected molecular characteristic or a selected range of molecular characteristics. In some such embodiments, an additional ion trap may be interposed between the first fragmentation stage and the first of the one or more ion separation instruments.

In still another example, one or more dissociation or fragmentation stages, regions or chambers and/or one or more ion traps may be interposed between any two ion separation instruments in any of the previous examples which include two or more ion separation instruments.

In each of the foregoing examples, ion separation, dissociation or fragmentation and/or trapping is carried out in the gas phase. In such example configurations which do not include a solvation stage, it will be desirable to solvate ions emerging from the last gas-phase stage $S_{M-1}$ so that the droplet generator 14 can generate droplets 40 from a sample solution. In such example configurations, the last sample source stage $S_M$ is accordingly a solvation stage configured to combine the solute, i.e., the ions emerging from the last gas-phase stage $S_{M-1}$, with a suitable solvent to form a sample solution 28 from which the droplet generator 14 can generate the droplets 40.

In other embodiments in which the sample source stage $S_1$ includes a sample solution 28 disposed in a sample container 30 as illustrated in FIG. 1, the sample stages $S_2$-$S_M$ may include one or more stages configured to separate molecules in the sample solution 28 prior to generating the droplets 40 with the droplet generator 14. As one example, the sample stages $S_2$-$S_M$ may include a gravity-fed liquid chromatograph (LC) column configured to separate molecules in the sample solution 28. As another example, the sample stages $S_2$-$S_M$ may include a conventional pump followed by a liquid chromatograph (LC) column configured to separate molecules in the sample solution 28. In such embodiments, the pump provides the motive force for advancing the solution 28 through the LC column. As yet another example, the LC column in either of the previous examples may be followed by a conventional static or dynamic mixing chamber. It will be understood that in any of the foregoing embodiments which include a solvation stage and/or instrument, the droplet generator 14 need not include ionization capabilities, and in other embodiments the droplet generator 14 may be omitted altogether.

In some embodiments of the instrument 100 illustrated in FIG. 2, an ion activation region (AR) 17 may be interposed between the molecule energizing stage 16 and the ion analyzer 18 as depicted by dashed-line representation in FIG. 2. In such embodiments, the ion activation region 17 may be provided in any conventional form and configured to controllably dissociate or fragment ions, e.g., via collision-induced dissociation (CID), surface-induced dissociation (SID), electron transfer dissociation (ETD), electron capture dissociation (ECD), photo-induced dissociation (PID) and any combination thereof. In embodiments which include the ion activation region 17, energized droplets 40 exiting the molecule energizing stage 16 are dissociated or fragmented therein prior to analysis with the ion analyzer 18. As will be described in detail with respect to FIGS. 9-14, inclusion of the ion activation region 17 allows the instrument 100 to identify at least partially unfolded particles which may not have been easily identifiable in their folded form and/or to more accurately determine abundances of different components of a particle than could otherwise be determined with the particle in its folded state.

In some applications of the instrument(s) 10, 100 illustrated in FIG. 1 and/or FIG. 2, melting analysis may be conducted with respect to molecules confined within droplets 40 of a solution 28. In some such applications, the molecules may be protein molecules in an aqueous solvent, although it will be understood that the instrument(s) and technique(s) described herein are not limited to proteins or to aqueous solvents, and in other applications the molecules may be or include any single-species molecule or multiple different molecule species in any type of solvent, aqueous or otherwise, examples of which may include, but are not limited to, one or any combination of a monomer, a homodimer, a heterodimer, a homotetramer, a heterotetramer and any homomultimer or heteromultimer. In some implementations of the instrument(s) 10 and/or 100, the droplet generator 14 may be configured to produce droplets of single protein molecules, i.e., each droplet contains a single protein molecule, although in other implementations the droplet generator 14 may be configured to produce droplets of multiple single-species or multi-species protein molecules.

In the embodiment illustrated in FIG. 1, charged droplets 40 are controlled, e.g., by an electric field E, to travel through a molecule energizing field 44 produced by a molecule energizing source 42, e.g., one or more lasers configured to produce radiation in the visible, infrared or other portion of the electromagnetic spectrum, in which the charged droplets are irradiated for a controllable time duration as they move from the molecule energizing stage 16 into and through the inlet 48 of the ion analyzer 18. The time duration may be controlled, e.g., by a processor 22, to be, for example, 0.01 to 10 milliseconds, although time durations outside of this example range are contemplated by this disclosure. The output power of the molecule energizing field 44 may fixed or may be variably controlled, e.g., by the processor 22. In any case, as the charged droplets are thermally excited in the presence of the field 44, the protein(s) in the irradiated droplets experience structural changes prior to solvent evaporation and ion formation.

This disclosure is not limited to molecule energizing sources which produce one or more molecule energizing fields of the type described above. Rather, in alternate embodiments any molecule energizing source may be implemented for inducing at least one structural change in at least one molecule contained in at least one of the droplets 40 generated by the droplet generator 14 prior to entry into the ion analyzer 18. In any such alternate embodiment, the molecule energizing source will be configured to produce an energy field and will be positioned relative to the nozzle orifice 38 of the droplet generator nozzle 36 such that the produced energy is applied to at least one of the generated droplets 40 exiting the droplet generator 14, and the produced energy field will be such that it induces at least one structural change in at least one molecule contained in the at least one of the generated droplets 40 prior to entry into the ion analyzer 18. The molecule energizing field generating source 42 illustrated in FIG. 1 and described above represents only one such molecule energizing source in the form of at least one laser configured to produce the molecule energizing field 44 in the form of a collimated radiation field which carries the produced energy, e.g., in the form of photons, into at least some of the generated droplets 40. Energy in the radiation carried by the molecule energizing field 44 redistributes into the motion of the molecules of the solution of at least one of the generated droplets 40 causing it to heat sufficiently to induce at least one structural change in at least one molecule contained in the at least one of the generated droplets 40.

Alternate molecule energizing stage embodiments may illustratively include at least one energy source configured to produce the molecule energizing field 44 in the form of a thermal energy field which heats at least one of the generated droplets 40 sufficiently to induce at least one structural change in at least one molecule contained in at least one of the generated droplets 40 prior to entry into the ion analyzer 18. Referring to FIG. 3A, for example, an alternate embodiment is shown of a molecule energizing stage 16' which includes one example embodiment of such an energy source in the form of a source of heated gas 60. In the illustrated embodiment, an outlet tube or cannula 62 couples the gas source 60 to the molecule energizing stage 16' such that the gas source 60 discharges a thermal energy field 64 in the form of a directed flow of heated gas into the path of the generated droplets 40 as shown. In one embodiment, the gas source 60 may be configured to discharge the thermal energy field 64 in the form of a jet of heated gas, and in other embodiments the gas source 60 may be configured to discharge the thermal energy field 64 in the form of a plume of heated gas. In some embodiments, a heating source 66, e.g., in the form of heating coils or other conventional heating source, may be controlled manually or by the processor 22 or other controller to control the temperature of the gas discharged by the gas source 60 and thus the temperature of the thermal energy field 64 directed into the molecule energizing stage 16'. In other embodiments, preheated gas may be supplied to the gas source 60 for discharge into the molecule energizing stage 16'. In either case, the flow, flow rate and/or the temperature of the thermal energy field 64, in the form of heated gas, into the molecule energizing stage 16' may be controlled manually or by the processor 22 or other controller.

Referring to FIG. 3B, another alternate embodiment is shown of a molecule energizing stage 16" which includes another example embodiment of a an energy source in the form of a source of heated tube or capillary 70 separate from the nozzle 36 of the droplet generator 14. In the illustrated embodiment, the tube or capillary 70 is positioned within the molecule energizing stage 16" such that a longitudinal axis defined through a passageway of the tube or capillary 70 is in-line with the longitudinal axes 35 and 45 illustrated in FIG. 1 so that droplets 40 moving under the influence of the electric field, E, (also illustrated in FIG. 1) are directed into, through and out of the tube or capillary 70 as illustrated in FIG. 3B. In other embodiments in the tube or capillary 70 may have other orientations relative to one or more components of the instrument 100. In any case, a heat source 72, e.g., in the form of one or more conventional heating coils or other conventional heat source(s), is illustratively coupled to the tube or capillary 70, and is controllable manually or by the processor 22 or other controller to control the temperature of the tube or capillary 70, thus creating a thermal energy field within the passageway of the tube or capillary 70 through which the droplets 40 move into the inlet 48 of the ion analyzer 18. In some embodiments, the tube or capillary 70 may illustratively be or include Carbon, although the tube or capillary 70 may be or include other material compositions in other embodiments. In any case, some embodiments may include one or more conventional cooling sources controllable manually or by the processor 22 or other controller to selectively cool the tube or capillary 70. Example cooling sources may be or include, but should not be limited to, one or more sources of ambient or cooled air directing air flow to or through the tube or capillary 70, liquid coolant circulating in contact with the tube or capillary 70 or the like.

Referring to FIG. 3C, another alternate embodiment is shown of a molecule energizing stage 16''' which includes an example embodiment of an energy source in the form of a conventional source 80 of microwave radiation. In the illustrated embodiment, a conventional wave guide 82 couples the microwave radiation source 80, e.g., in the form of a conventional magnetron (MAG), to the molecule energizing stage 16''' such that microwave radiation 84 produced by the source 80 is guided by the wave guide 82 into the path of the generated droplets 40 as shown. In embodiment illustrated in FIG. 3C, the direction of the microwave radiation field 84 is illustratively controlled by the waveguide 82 to be perpendicular to the direction of the electric field E (illustrated in FIG. 1), although in other embodiments the waveguide 82 may be positioned or designed to direct the microwave radiation field in a non-perpendicular direction relative to the direction of the electric field E. In any case, energy in the radiation carried by the microwave radiation field 84 redistributes into the motion of the molecules of the solution of at least one of the generated droplets 40 causing it to heat sufficiently to induce at least one structural change in at least one molecule contained in the at least one of the generated droplets 40 prior to entry into the ion analyzer 18. The power, duration, duty cycle and/or other characteristic of the microwave radiation field 84 produced by the microwave radiation source 80 may be controlled manually or by the processor 22 or other controller.

Still other alternate molecule energizing stage embodiments are contemplated by this disclosure in which the produced energy induces a chemical reaction within the at least one of the generated droplets 40, and the induced chemical reaction within at least one of the generated droplets 40 results in the at least one structural change in at least one molecule contained therein.

In some embodiments, the output power of the molecule energizing source 42, 60, 70, 80 may be varied, and by varying the output power the resulting temperature of the affected droplets 40 can be defined with precision and accuracy. When compared with transitions induced by thermally heating solutions prior to droplet formation, the shapes of melting curves as a function of molecule energizing source power can be calibrated to an effective droplet temperature ($T_{eff}$) and derived melting temperatures as well as shifts induced by changing the solution pH (or concentrations of other species) can, in turn, be obtained. The ability to induce structural transitions in droplets that resemble those found upon heating bulk solution alleviates the lengthy time requirements for solution heating in conventional systems.

It will be understood that this disclosure is not limited to molecule energizing sources operable to induce at least one structural change in at least one molecule contained in at least one of the droplets 40 generated by the droplet generator 14. Rather, this disclosure contemplates alternate embodiments in which one or more molecule energizing sources, e.g., in the form of one or more conventional heaters or one or more conventional heating elements, is/are configured to induce at least one structural change in at least one molecule contained in the sample solution 28 prior to generation by the droplet generator 14 of the droplets 40 and/or as the droplets 40 are being generated by the droplet generator 14. At least one of the droplets 40 generated by the droplet generator 14 will thus contain at least one molecule in which at least one structural change has been induced. In the former case, the one or more molecule energizing sources may, for example, be configured and positioned to heat the sample container 30 and thereby heat the sample solution 28, to heat the tube or capillary 34 and thereby heat the sample solution 28 supplied thereby to the droplet generator 14 and/or to heat the pump 32 and thereby heat the sample solution 28 contained therein. In the latter case, the one or more molecule energizing sources may be configured and positioned, for example, to heat the capillary or nozzle 36 to thereby heat the sample solution 28 contained therein as the droplets 40 are being generated. In any case, the temperature(s) of the one or more conventional heaters and/or one or more conventional heating elements may be controlled manually or by the processor 22 or other controller.

The ability to induce melting transitions in individual droplets has transformative potential to a number of areas in the field of structural biology, as it allows for melting temperatures of individual species found in complex mixtures to be rapidly characterized using conventional ion analysis instruments 18. Moreover, the possibility of high-throughput characterization of protein stabilities has substantial potential in the field of structural biology, making it possible to build libraries of information that will ultimately be valuable as an additional biophysical property (used for characterizing known systems) as well as presenting new opportunities for predicting stabilities for unknown systems.

Additionally, studies of single molecules in droplets make it possible to investigate systems that aggregate upon denaturation. For example, many systems aggregate upon heating, making it impossible to study the stability of the precursor monomers or complexes. But by isolating species inside of individual droplets as described above, it is possible to investigate structures, structural transitions, and stabilities in the absence of aggregation. With regard to investigation of structural transitions, for example, protein melting transitions are conventionally characterized as cooperative two-state processes; that is, from a folded state to has been assumed to be a complex distribution of amorphous unstructured species. However, experiments undertaken with the instrument(s) 10, 100 described above have demonstrated (as described in the examples below) that this cooperative process in some cases is actually a composite and a progression of multiple transitions, from several precursors that lead to numerous products. In particular, as single-protein droplets are exposed to a molecule energizing field 44, 64, 84 or are exposed to other thermally controlled conditions, a progression of numerous intermediate equilibrium structures are observed with increasing field power or other increasing temperature condition(s), wherein each such intermediate equilibrium structure is stable at different respective temperature. The instrument(s) 10, 100 thus make it possible to detect structural transitions that have not been observed previously in a high-throughput analysis environment capable of characterizing melting temperatures for individual species present in mixtures. Such analysis techniques naturally extend to studies of species that vary in post-translation modification type as well as position, protein complexes, and as well as species that are notoriously difficult to study because of issues of solubility.

Although the following examples focus on techniques for characterizing proteins, protein complexes and proteomes, the approach will be understood to be general in that it is expected to be useful for the evaluation of many different types of biopolymers. Information about the stabilities and dynamics of large numbers of biomolecules using the instrument(s) 10, 100 has transformative potential and is expected to have utility as a benchmark connecting fundamental problems (e.g., theoretical efforts to calculated structural properties) with applied routine problems (e.g., is an expressed therapeutic molecule folded properly). The instrument(s) 10, 100 and techniques described herein will enable insight into how post-transitional modifications, binding interactions (e.g., protein-protein or protein-ligand), and environment influence molecular structures and stabilities. The determination of kinetic and thermodynamic properties such as folding/unfolding rates and melting temperatures will find broad applications from many types of problems, e.g., as analytical constraints illuminating how changing environments influence physical properties, to a broad new understanding of the interplay between ligand binding, substrate structures, and stabilities, all essential to understanding issues, e.g., such as on target and off target binding interactions, which are key to characterizing new therapeutics.

The following examples are provided for the purpose of demonstrating some useful methods which may be employed with particular structural embodiments of the instrument(s) 10, 100. It will be understood that such methods and/or particular structural embodiments are merely exemplary in nature, and should be considered to be exhaustive or limiting in any way. While several of the following examples are described as being carried out using the instrument of FIG. 1, it will be understood that the instrument 100, in any of its various forms described above, may alternatively be used.

Example 1

The ability to determine melting transitions by thermal excitation of droplets makes it possible to determine melting temperatures for unknowns which may be subsequently identified by conventional ion analysis strategies. Moreover, when single molecules in droplets are melted as the droplets pass through thermal excitation fields of varying intensity temperature, as described above, changes are induced instantly without influencing any other experimental parameter(s). This approach allows for high-throughput melting transition measurements.

Figure 4:
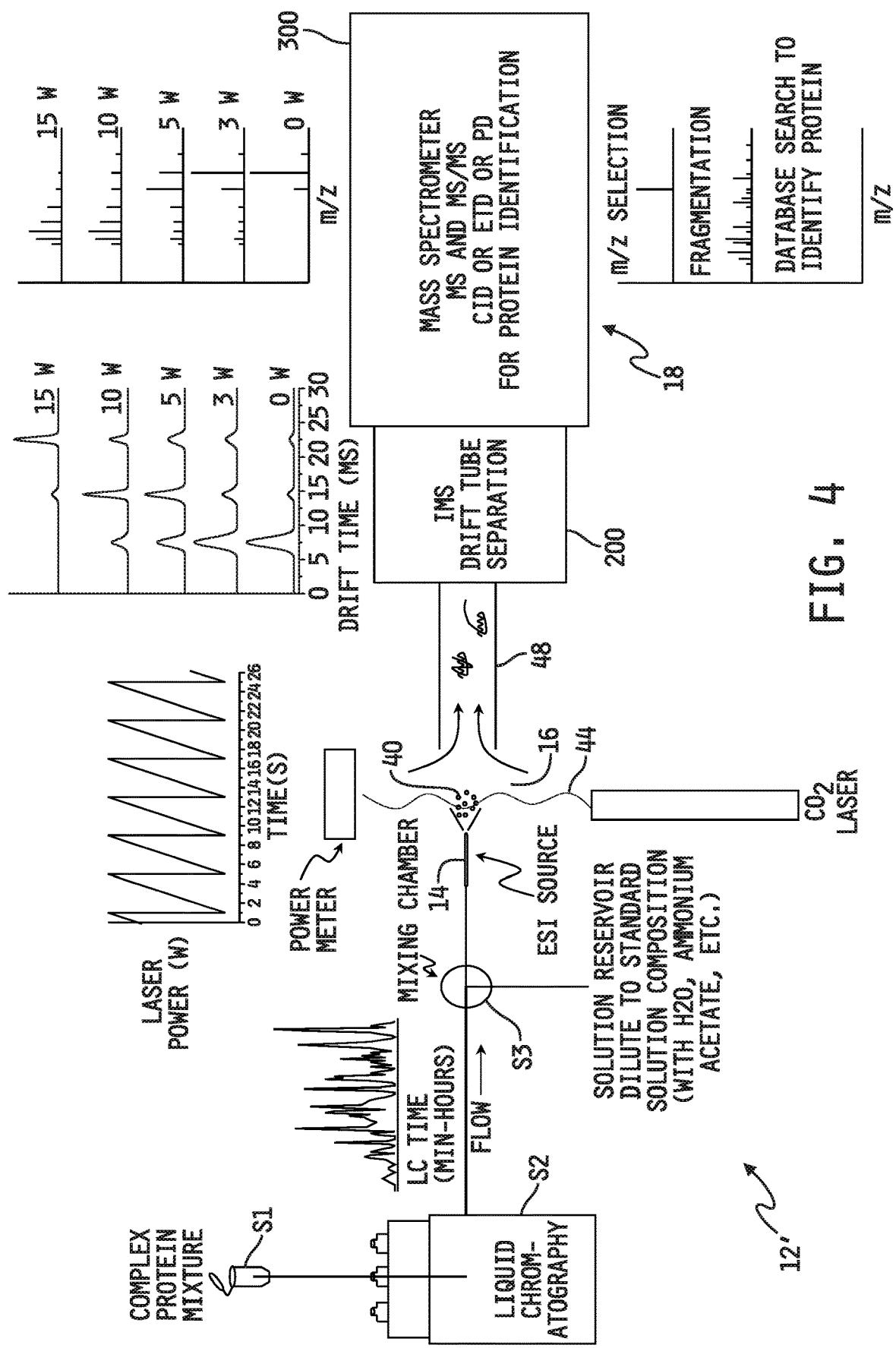
FIG. 4 illustrates a specific example of the instrument illustrated in FIG. 2 for conducing high-throughput melting transition measurements.

Referring to FIG. 4, an example implementation 100' of the generalized instrument 100 illustrated in FIG. 2 is shown. In the example illustrated in FIG. 4, the sample source 12' is a three-stage sample source which includes a high performance liquid chromatography (HPLC) column $S_2$ into which a solvent $S_1$ containing a complex protein mixture is fed, and in the illustrated example separated mixture components exiting the HPLC column $S_2$ are collected and mixed in a mixing chamber $S_3$. The mixing chamber $S_3$ supplies its contents to the nozzle of a droplet generator 14 in the form of an ESI unit, and droplets 40 produced by the droplet generator 14 pass, under the influence of an established electric field, through the molecule energizing stage 16. The molecule energizing stage 16 illustratively includes a $CO_2$ infrared laser as the molecule energizing source, and droplets 40 moving through the molecule energizing stage 16 are irradiated by the molecule energizing field 44 produced by the laser. The irradiated droplets 40 pass under the influence of the electric field into the inlet capillary 48 of the ion analyzer 18 illustratively provided in the form of a cascaded arrangement of an IMS 200 followed by a two-stage MS-MS instrument 300.

In the example illustrated in FIG. 4, the instrument 100' is used to determine thermally induced structural transitions and melting temperatures for a complex mixture of proteins, e.g., such as those encountered in proteomics workflows. In this approach, as proteins elute from the HPLC column $S_2$ they are introduced into mixing chamber $S_3$ where known fractions of eluent are diluted into a standard solution, and then electrosprayed by the ESI source 14. The radiation intensity of this source is illustratively controlled by a motorized polarizing filter allowing the excitation power to be scanned from 0 to 25 W in short time periods (e.g., 10 s per 0-25 W power scan). The 10 s per power scan time is much shorter than chromatographic elution times (typical peak FWHM ~30 to 60 s) allowing replicate measurements to be made for each eluting species being studied; although it should be understood that 10 s per scan is much longer than the analysis time required by the ion analyzer 18. In the illustrated example, nested IMS-MS datasets produced by the ion analyzer 18 are used to understand structural transitions and provide melting profiles. Data dependent MS selection and activation of precursor protein ions are used to produce 'top-down'-MS-MS information for protein identification. With the instrument 100', it is possible to determine the stabilities of hundreds of different proteins in a single experiment. Even if a protein is not unambiguously assigned, the instrument 100' will produce melting temperatures, precursor m/z values, as well as cross section information for these species, and such stability information may provide insight about why some proteins are more amenable to top-down analysis than others.

Example 2

The instrument 10 illustrated in FIG. 1 is used in this example, in which the ion analyzer 18 is provided in the form of a cascaded arrangement of an IMS-IMS instrument followed by a MS-MS instrument. An electric field, E, established by the power source 50 draws the droplets 40 exiting the ESI nozzle 36 toward the inlet capillary 48 of the ion analyzer 18. The molecule energizing source 42 is an infrared (10.6 μm) laser having variable (controllable) power output. Aqueous 10 μM aqueous solutions of ubiquitin (or other proteins) are electrosprayed from capillary emitters having orifice diameters ranging from 0.5-50 μm. The emitter tips are illustratively aligned to, and positioned defined distances away from, the inlet capillary 48 of the ion analyzer 18. The droplet diameters are estimated to be a fraction (1/20) of the emitter orifice diameter. Charged droplets containing 1 protein molecule pass through the $CO_2$ laser field focused adjacent to the inlet capillary 48. Activation in this region by the molecule energizing field 44 induces structural changes in some of the proteins within some of the droplets 40 which leads to changes in the protein charge state distribution and ion structures. This instrument is also equipped with a ZnSe laser window in the middle of the drift tube. Irradiating single molecules of ubiquitin confined within small (~0.01 to ~0.2 μm dia.) charged droplets produced by electrospray ionization with 10.6 μm light of varying intensity (0-20 W), produces melting transitions prior to droplet evaporation and ion formation. These transitions are dependent upon droplet size, e.g., smaller droplets require exposure to higher intensity light than larger droplets, and no structural changes are induced upon irradiation of naked ions. When the pH of the protein solution decreases, transitions within the droplets are observed at lower laser powers, indicating that the chemical environment couples to the unfolding transition prior to solvent evaporation and ion formation. The approach appears to be useful for many proteins; laser intensity profiles, i.e., laser output profiles, associated with transitions in droplets can be calibrated or mapped to melting temperatures ($T_m$) obtained from traditional calorimetric and spectroscopic methods such that the approach can be used to characterize the stabilities of species where no species identification information exists. Studies of solution transitions, by monitoring the structures of ions with gas-phase measurements such as ion mobility spectrometry (IMS) and mass spectrometry (MS), are likely to find many applications, including: determination of $T_m$ values for low abundance species, individual species in mixtures, as well as unknown species that are subsequently identified by fragmentation analysis (see, e.g., examples below with reference to FIGS. 9-14); characterization of species that aggregate in bulk solution at elevated temperatures; and, the determination of shifts in melting temperature upon ligand-, metal ion-, or substrate-binding, and the like.

Figure 5A:
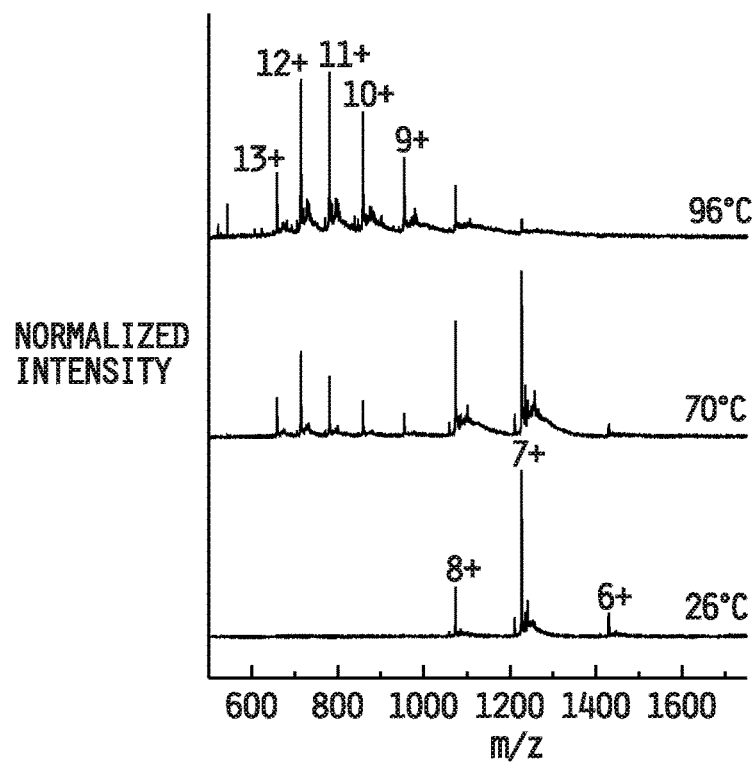
FIG. 5A is a mass spectral plot obtained upon thermal heating of an aqueous ubiquitin solution (pH 3.0) for approximately 8 minutes in an ESI source at 26, 70 and 96 degrees C., showing the effect of solution temperature on charge state distribution for the ubiquitin ions.
Figure 5B:
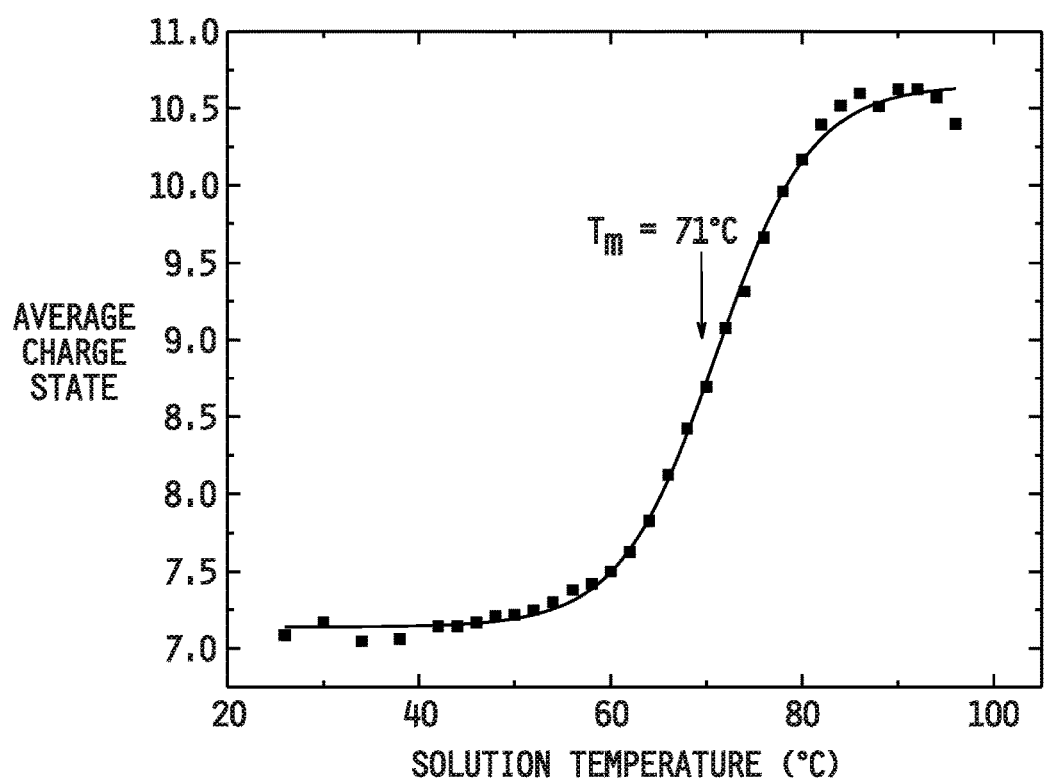
FIG. 5B is a plot of weighted average charge state vs. solution temperature for the solution data of FIG. 5A, illustrating a melting temperature of approximately 71 degrees C.

By way of reference, FIG. 5A shows mass spectra obtained upon thermal heating of an aqueous ubiquitin solution (pH~3) for ~8 min in an ESI source at 26, 70, and 96° C. At 26° C., the charge state distribution favors the [M+7H]7+ species, consistent with a "native" ESI mass spectrum for a protein. As the solution temperature is increased to 70° C., new peaks corresponding to highly charged ubiquitin ions is observed, which are a direct result from thermal unfolding of the native ubiquitin protein to expose buried basic residues. These ions, centered around the [M+11H]11+ charge state, completely dominate the mass spectrum at 96° C. The plot in FIG. 5B shows weighted average charge state as a function of solution temperature, which is fit to a sigmoidal two-state unfolding model to yield the melting temperature of 71±2° C. This value is in good agreement with prior calorimetric and spectroscopic studies.

Figure 5C:
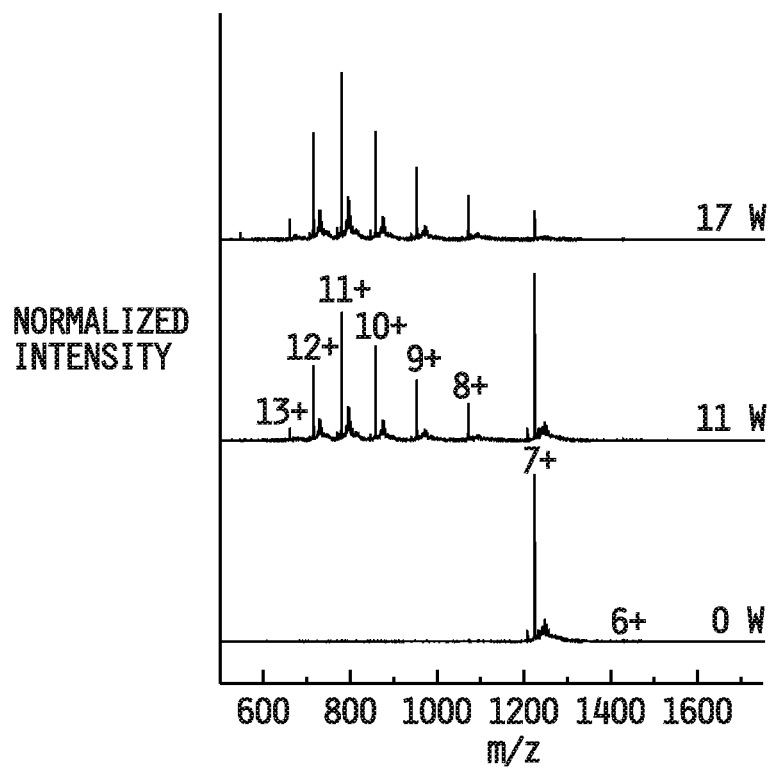
FIG. 5C is a mass spectral plot of the same solution as used in FIGS. 5A and 5B in which droplets of the solution were irradiated with a 10.6 µm $CO_2$ laser operating at each of 0, 11 and 17 Watts.
Figure 5D:
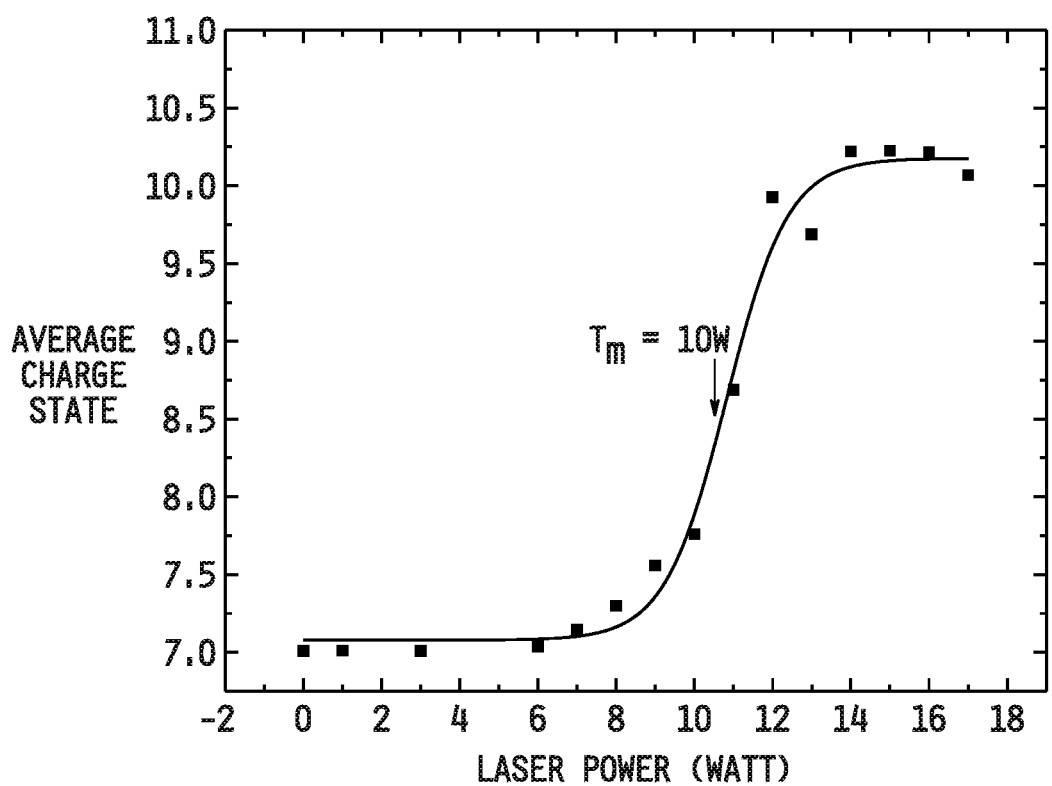
FIG. 5D is a plot of weighted average charge state vs. laser power for the irradiated solution data of FIG. 5C, illustrating a laser-induced melting temperature of ubiquitin correlated to approximately 10 Watts of laser power.

By way of comparison, FIG. 5C shows mass spectra obtained upon thermal excitation of electrospray droplets 40 originating from the same ubiquitin solution by laser irradiation at 0, 11, and 17 W using the instrument of FIG. 1 described above. At 0 W, the charge state distribution is again dominated by the [M+7H]7+ ion, indicating the folded, native state is the predominant solution structure. At 11 W, the mass spectrum shows the emergence of several highly charged ions, centered around the [M+11H]11+ ion, indicating that a substantial fraction of the population exists in the unfolded state. These ions dominate the spectrum at 17 W, which shows that the droplet lifetimes are sufficient to facilitate unfolding prior to droplet evaporation. The weighted average charge state plot shown in FIG. 5D illustrates that the relationship between laser power and folded/unfolded fraction(s) can be treated with a two-state model to obtain a melting "wattage," e.g., in this case approximately 10 W.

Example 3

Figure 6A:
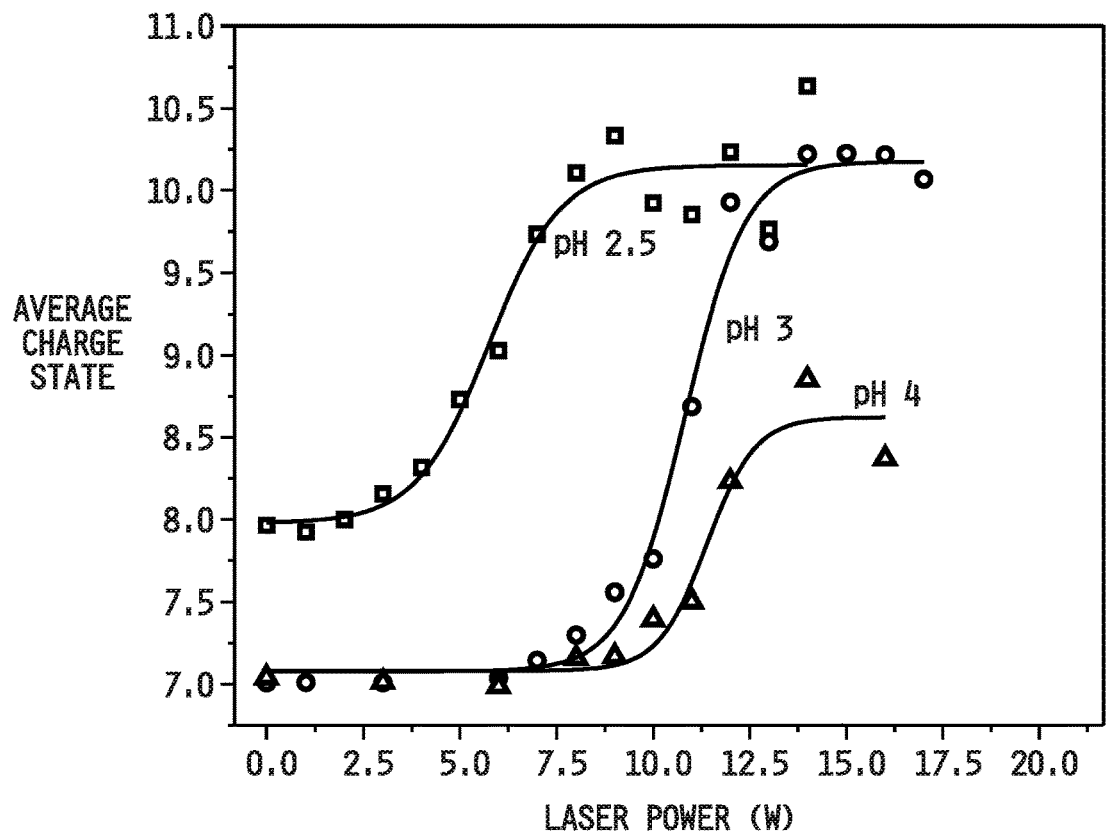
FIG. 6A is a plot of average charge state vs. laser power showing melting curves for ubiquitin in solutions of 2.5 pH, 3 pH and 4 pH using the instrument 10 illustrated in FIG. 1.

This example demonstrates how laser-induced unfolding transitions can be influenced by the environment of the droplet; in this case, with changes in solution pH. For example, FIG. 6A shows the weighted average charge states obtained for ubiquitin in confined in droplets 40 produced from solutions maintained at pH=4.0, 3.0, and 2.5. In this example, the instrument and instrument parameters are as described above in Example 2.

Figure 6B:
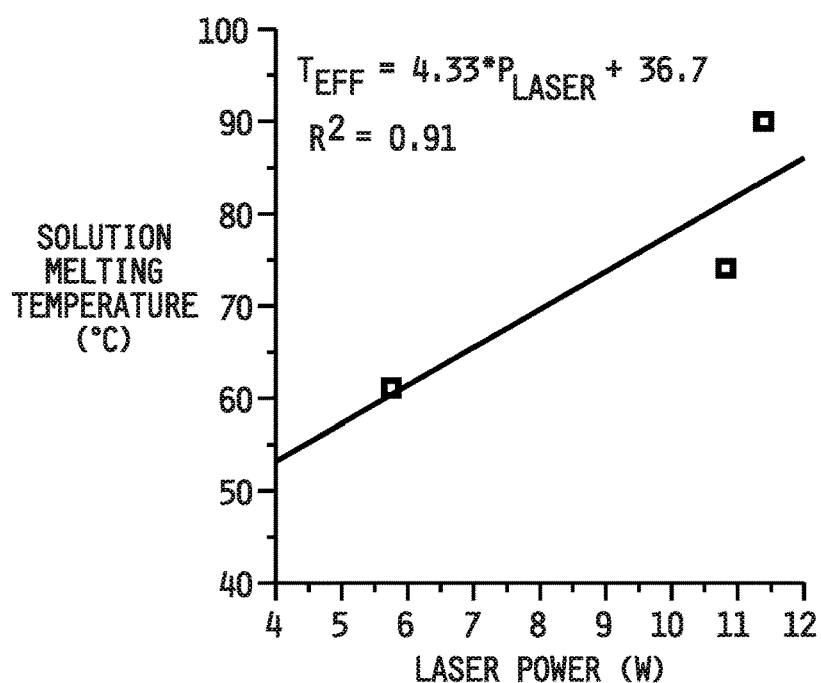
FIG. 6B is a plot of solution melting temperature vs. laser power showing an approximate linear relationship between the melting temperatures of the three solutions of FIG. 6A and corresponding laser power.

At pH 2.5, a small fraction of the unfolded state is already populated, as shown by the presence of the highly charged ions in the mass spectrum obtained at 0 W. These unfolded ions already dominate the mass spectrum at 12 W, indicating that the droplet retains a "memory" of the bulk solution pH. The pH 4 solution shows the folded state as the dominant population at 0 W, and remains the dominant population until 14 W. In each case, an increase in laser intensity causes the folded states to decay, and the unfolded species to emerge. The midpoints associated with these transitions shifts to lower laser powers with decreasing solution pH, thus corroborating the idea that the environment of the droplet is mimicking that of the bulk solvent. The similarities observed between thermal unfolding by solution heating and by heating electrospray droplets 40 by infrared laser irradiation suggests that it may be possible to calibrate the droplet unfolding with data obtained for thermal unfolding in solution immediately prior to ESI. As illustrated by example in FIG. 6B, the melting transition of the pH 2.5 solution at approximately 5.1 Watts correlates to a melting temperature of approximately 62° C., the melting transition of the pH 3.0 solution at approximately 10.5 Watts correlates to a melting temperature of approximately 75° C. and the melting transition of the pH 4.0 solution at approximately 12 Watts correlates to a melting temperature of approximately 90° C.

Example 4

Another technique for assessing the nature of structural transitions in a droplet is to examine two protein molecules having different known melting temperatures emerging from the same solution. In this example, the instrument and instrument parameters are as described above in Example 2.

Figure 7A:
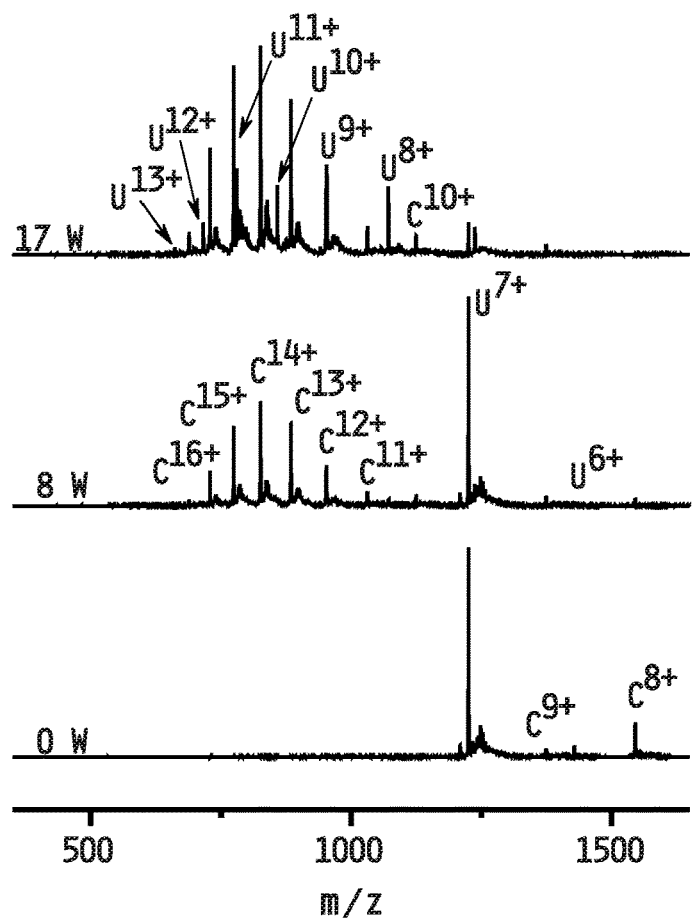
FIG. 7A is a mass spectral plot of a pH 3.0 solution containing a mixture of cytochrome c and ubiquitin in which droplets of the solution were irradiated with a 10.6 µm $CO_2$ laser operating at 0, 8 and 17 Watts using the instrument of FIG. 1.
Figure 7B:
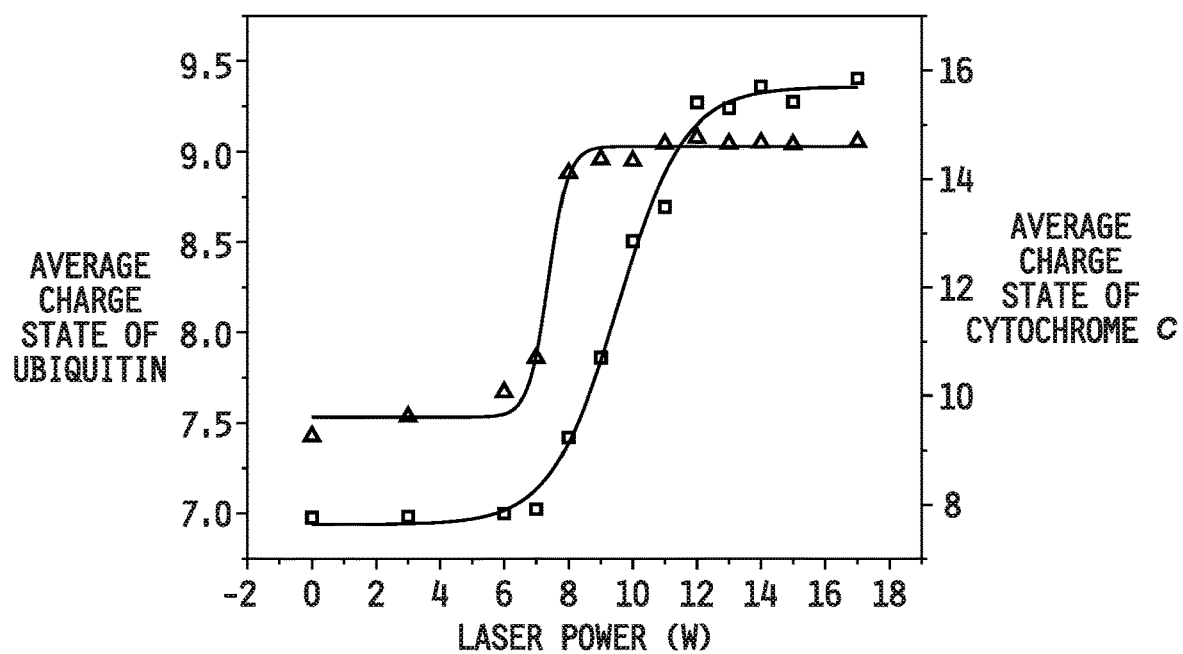
FIG. 7B is a normalized 2-state plot of average charge state vs. laser power demonstrating the lower melting temperature (and lower corresponding laser power of approximately 7.4 Watts) of cytochrome c (triangles) as compared to the melting temperature (and corresponding laser power of approximately 9.2 Watts) of ubiquitin (squares).

FIGS. 7A-7B show the results obtained upon irradiating droplets produced from a pH=3.0 solution containing a mixture of ubiquitin, where $T_m$=72° C., and equine cytochrome c having $T_m$=48° C. With no laser irradiation, the charge state distribution is centered around $[M+7H]^{7+}$ for ubiquitin, and $[M+8H]^{8+}$ for cytochrome c. When the droplets are irradiated with 8 W, the charge state distribution of cytochrome c shifts such that it is centered about the $[M+14H]^{14+}$ species, while the average charge state of ubiquitin remains unchanged; this indicates that cytochrome c has unfolded while ubiquitin has not. At 17 W, both ubiquitin and cytochrome c have unfolded. The weighted average charge state vs laser power plot of FIG. 7B further illustrates that the melting transitions of ubiquitin and cytochrome c (at laser powers of 9.2 Watts (squares) and 7.4 Watts (triangles) respectively) are independent of one another, and correlate with the expectation that cytochrome c should denature at a lower temperature as compared to ubiquitin at pH 3.0. These results illustrate two points: the appropriate melting profiles for each protein indicates that the environment appears to be accessible to both proteins; additionally, it should be noted that this approach is well suited for the analysis of mixtures which present complications for traditional methods.

Example 5

Figure 8A:
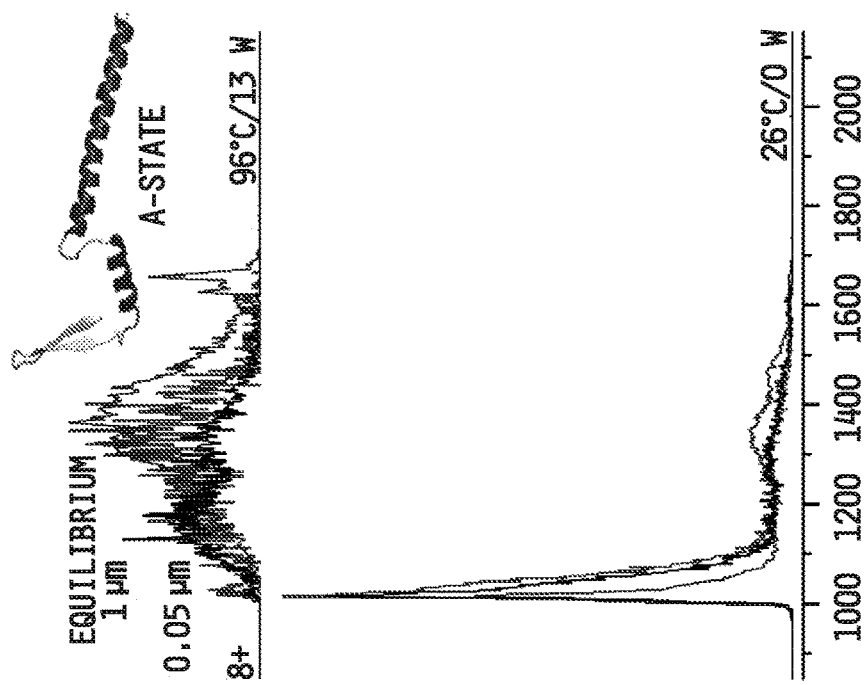
FIG. 8A is plot of cross-section distributions for $[M+7H]^{7+}$ ions of ubiquitin at two different solution temperatures and laser powers demonstrating correlation between melting temperature measurements via control of solution temperature and via laser radiation using the instrument of FIG. 1.
Figure 8B:
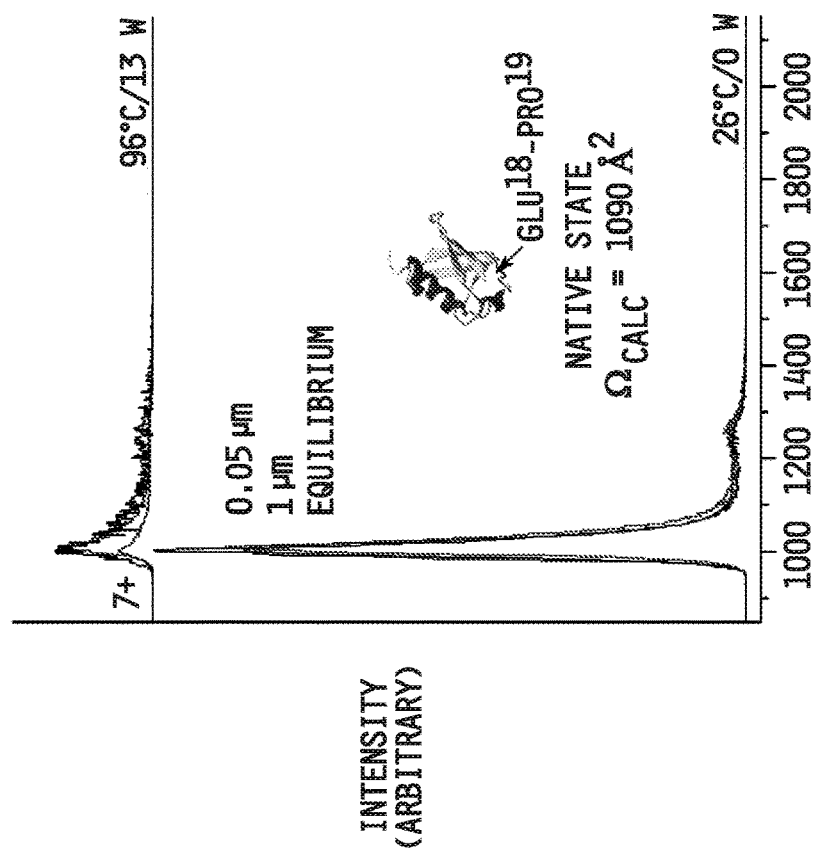
FIG. 8B is plot of cross-section distributions for $[M+8H]^{8+}$ ions of ubiquitin at two different solution temperatures and laser powers demonstrating correlation between melting temperature measurements via control of solution temperature and via laser radiation using the instrument of FIG. 1.
Figure 8C:
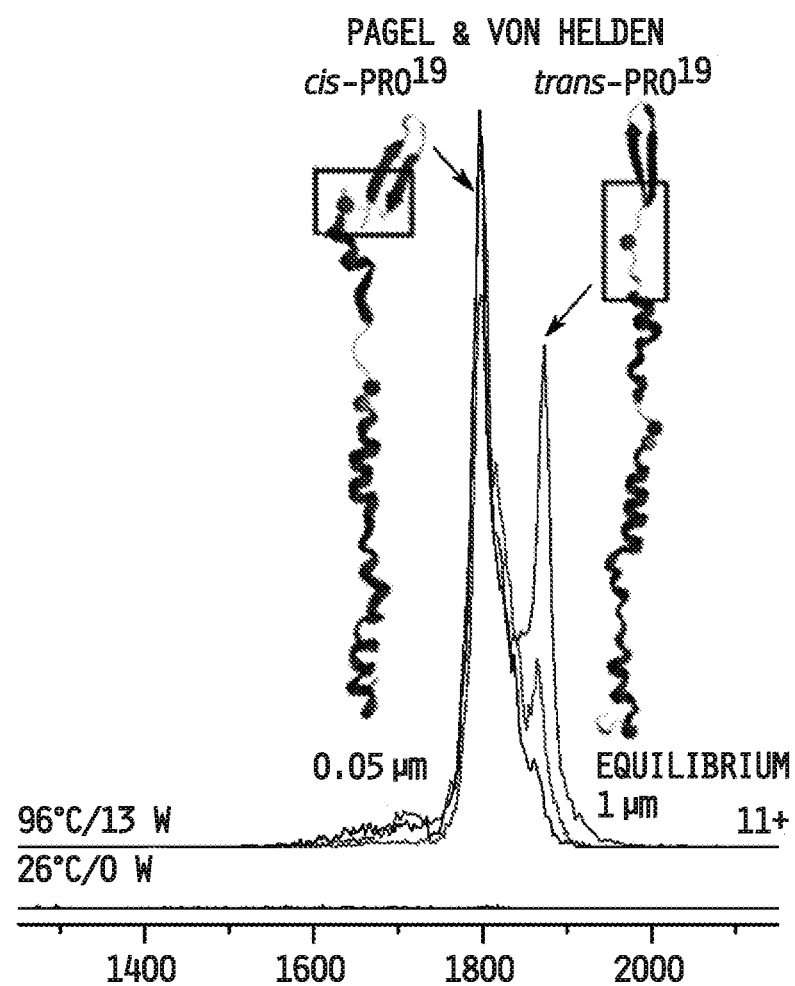
FIG. 8C is plot of cross-section distributions for $[M+11H]^{11+}$ ions of ubiquitin at two different solution temperatures and laser powers demonstrating correlation between melting temperature measurements via control of solution temperature and via laser radiation using the instrument of FIG. 1.

FIGS. 8A-8C show IMS cross section distributions for structural transitions involving the [M+7H]7+(FIG. 8A) and [M+8H]8+(FIG. 8B) precursor charge states, and one product ion, [M+11H]11+(FIG. 8C) formed by heating a ubiquitin solution to 26 and 96° C. as well as upon irradiating single molecules in droplets from the same solution with laser powers of 0 and 13 W (which correspond to calibrated temperatures of ~35 and 92° C.). In this example, the instrument and instrument parameters are as described above in Example 2.

Comparison of cross section distributions for [M+7H]7+ shows a single peak centered at Ω=1010 Å2, consistent with highly-folded structures expected for ions produced from solutions favoring the native state. Upon increasing either the solution temperature or the laser power used to irradiate droplets, we find that this peak decreases in relative abundance. A comparison of the decreases in abundances of the Ω=1010 Å2 peak, which yielded a value of Tm=72±2° C. from heated solution studies, shows that irradiating ubiquitin in droplets results in an indistinguishable decrease. Thus, the loss of the [M+7H]7+ species from droplets behaves as a melting transition.

While the cross section distributions [M+7H]7+ species profiles from droplets is consistent with solution melting transitions, cross section distributions for other charge state show marked differences. At 26° C., the [M+H]8+ species exhibits a sharp peak at Ω=1010 Å2. When the bulk solution of ubiquitin is heated this peak decreases in intensity and two broad features, which increase in relative abundance from T~45 to 60° C. and then decrease above T~70° C. (ascribed to equilibrium intermediates) are formed. A systematic increase is observed in the two sharp peaks at Ω=1635 and 1650 Å2 which have been assigned to the ubiquitin A state, a low abundance product of melting. While the A state may be somewhat unexpected, it should be noted that as the temperature is increased from ~26 to 96° C., the dielectric constant of water decreases from 78 to 56, near the value of 52 for a 40:60 water:methanol solution which favors the A state at 26° C. No evidence for the A state is observed from droplets. This suggests that this product cannot form during the short time after irradiation.

Example 6

It is observed that droplet transitions appear to be highly dependent on droplet size. It is possible to produce intermediate and small droplets by modifying electrospray emitters to various inner diameters to rigorously test the hypothesis that droplet size correlates to the extent of energy deposition. MS data and IMS distributions obtained by irradiating ca. 100 nm droplets (produced by a ~1.7 μm ESI emitter) as a function of laser power show that the proteins in these droplets appear to melt. When smaller droplets, formed by ESI at longer distances (~1 cm) are irradiated with IR light, the transitions require greater thresholds to produce unfolded, highly charged ions and do not appear to go to completion.

Example 7

Yet another application of the instrument 100 illustrated in FIG. 2 is the identification of unknown particles and abundance determinations of fragments of thereof. In this example, the ion activation stage 17 is included in the instrument 100. In the molecule energizing stage 16, at least one structural change is induced in at least one molecule contained in at least one of the droplets 40 generated by the droplet generator 14 as described above, the resulting structurally changed molecule is then dissociated in the ion activation stage 17 and the fragment(s) are then analyzed using the ion analyzer 18. This application provides for identification of unknown precursor particles via identification of at least one fragment thereof and/or provides for abundance determinations of one or more fragments of precursor particles.

Figure 9:
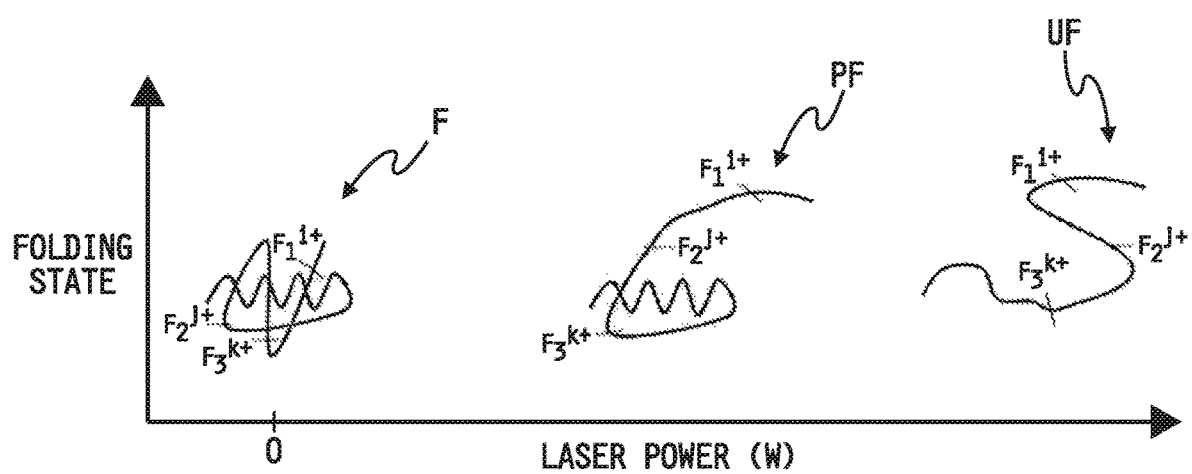
FIG. 9 is a simplified plot of folding state vs. laser power illustrating progressive unfolding of a precursor protein particle ($P^{n+}$) from a folded state (F), to a partially folded (or partially unfolded) state (PF), to a fully unfolded state (UF) with increasing laser power using the instrument of FIG. 1 or FIG. 2.
Figure 10:
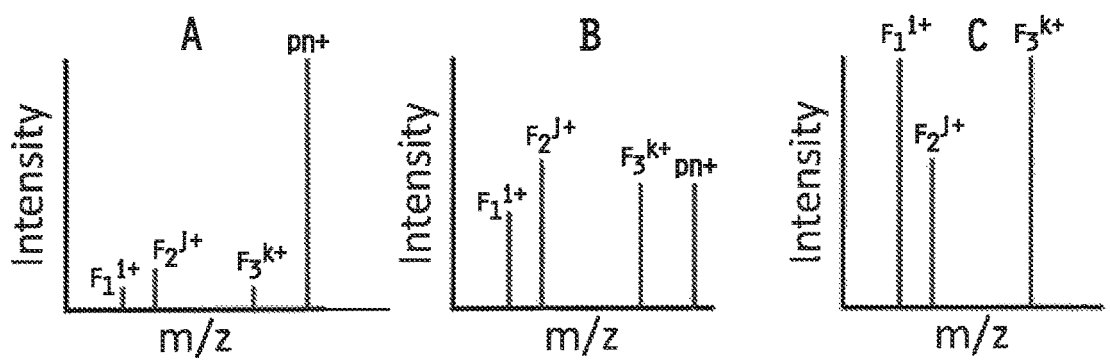
FIG. 10A is a plot of ion intensity vs. mass-to-charge ratio (m/z) illustrating intensities of the precursor particle of FIG. 9 and fragments thereof following dissociation of the precursor particle in its folded state (F) using an embodiment of the instrument of FIG. 2.
FIG. 10B is a plot of ion intensity vs. mass-to-charge ratio (m/z) illustrating intensities of the precursor particle of FIG. 9 and fragments thereof following dissociation of the precursor particle in its partially unfolded state (PF) using an embodiment of the instrument of FIG. 2.
FIG. 10C is a plot of ion intensity vs. mass-to-charge ratio (m/z) illustrating intensities of the fragments of the precursor particle of FIG. 9 following dissociation of the precursor particle in its fully unfolded state (UF) using an embodiment of the instrument of FIG. 2.
Figure 11:
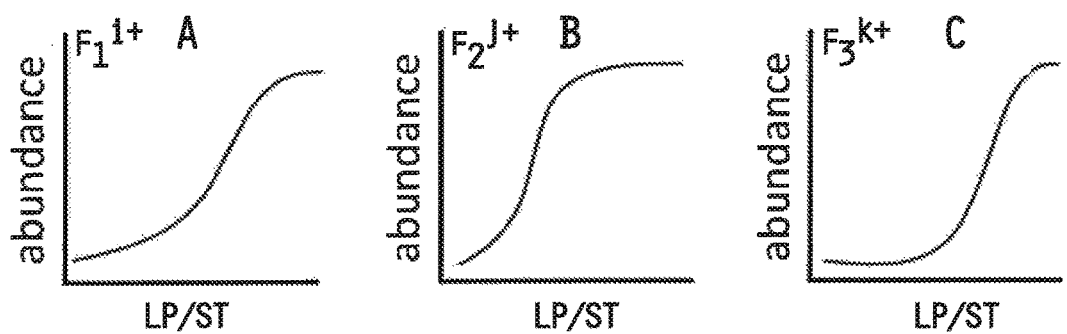
FIG. 11A is a plot of abundance vs. laser power (LP) or solution temperature (ST) illustrating abundance intensity of the protein fragment $F_1^{i+}$ of FIGS. 9 and 10A-10C as a function of increasing laser power or solution temperature.
FIG. 11B is a plot of abundance vs. laser power (LP) or solution temperature (SP) illustrating abundance intensity of the protein fragment $F_2^{j+}$ of FIGS. 9 and 10A-10C as a function of increasing laser power or solution temperature.
FIG. 11C is a plot of abundance vs. laser power (LP) or solution temperature (SP) illustrating abundance intensity of the protein fragment $F_3^{k+}$ of FIGS. 9 and 10A-10C as a function of increasing laser power or solution temperature.

Referring to FIG. 9, a simplified plot is shown of molecule folding state vs. laser power for an example precursor particle. At a laser power of zero Watts, the precursor particle is completely folded (F). As laser power is increased, the precursor particle begins to unfold as described above. The center precursor particle, for example, is partially folded (or unfolded) (PF), and the right-most precursor particle is completely or fully unfolded (UF). For purposes of this disclosure, the terms "folded" and "completely folded" are synonymous and are the gas-phase corollary of the "native state" of the precursor particle in solution. In the gas phase, the folded state of the precursor particle is the minimum or most compact or condensed cross-sectional conformation of the precursor particle. The terms "unfolded," "completely unfolded" and "fully unfolded" are synonymous and are the gas-phase corollary of the "denatured" state of the precursor particle in solution.

In the gas phase, the unfolded state of the precursor particle is the maximum or most expanded, uncondensed or outspread cross-sectional conformation of the precursor particle. The terms "partially folded" and "partially unfolded" are likewise synonymous and correspond, in the gas-phase, to one or more states of unfolding of the precursor particle between its folded and unfolded states. As described above, it has been observed using the instruments and techniques described herein that precursor particles may have multiple, progressive, discrete states of partial unfolding between the folded state (F) and the completely or fully unfolded state (UF) as a function of increasing laser power, and some or all such intermediate unfolded states may be stable at their respective temperature. As also described above, the precursor particle may be or include one or any combination of a monomer, a homodimer, a heterodimer, a homotetramer, a heterotetramer and/or any homomultimer or heteromultimer, and specific examples may be or include proteins, peptides, polypeptides, and the like.

Referring to FIGS. 10A-10C, plots of intensity vs. mass-to-charge ratio (m/z) are shown, each of which represents the m/z measurement of the ion analyzer 18 following dissociation and ion analysis of the precursor particle illustrated in FIG. 9 in each respective state of unfolding. Thus, FIG. 10A represents the m/z spectrum of the precursor particle of FIG. 9 dissociated in the activation region 17 of the instrument 100 while in its folded state (F), FIG. 10B represents the m/z spectrum of the precursor particle of FIG. 9 dissociated in the activation region 17 of the instrument 100 while in its partially folded state (PF), and FIG. 10C represents the m/z spectrum of the precursor particle of FIG. 9 dissociated in the activation region 17 of the instrument 100 while in its unfolded state (UF). As depicted in FIG. 10A, dissociation of the folded precursor particle pn+ leaves most of the precursor particle pn+ intact. With the precursor particle partially unfolded (PF) via the molecule energizing stage 16 as illustrated in FIG. 9, the precursor particle pn+ is diminished in intensity by approximately ½ as compared with FIG. 10A, and prominent intensity peaks of the fragments $F_1^{i+}$, $F_2^{j+}$ and $F_3^{k+}$ have emerged, each at different, distinct m/z values. With the precursor particle fully unfolded (UF) via the molecule energizing stage 16 as illustrated in FIG. 9, the precursor particle pn+ is no longer detectable, and strong intensity peaks of the fragments $F_1^{i+}$, $F_2^{j+}$ and $F_3^{k+}$ predominate.

Referring to FIGS. 11A-11O, abundances of the fragments $F_1^{i+}$, $F_2^{j+}$ and $F_3^{k+}$ respectively are plotted against laser power LP (or solution temperature ST). The abundance of each fragment $F_1^{i+}$, $F_2^{j+}$ and $F_3^{k+}$ increases with increasing laser power (or solution temperature), which is also demonstrated progressively in FIGS. 10A-10C. As also shown in FIGS. 11A-11O, the melting transitions of the various fragments $F_1^{i+}$, $F_2^{j+}$ and $F_3^{k+}$ are mapped to respective laser power (or solution temperature) values, and may thus be correlated to respective melting temperatures as described above in the previous examples.

In some embodiments of this example, the identity of the precursor particle pn+ may not be known, and may be identified only by one or more fragments thereof following fragmentation of the precursor particle in a partially or fully unfolded state. In other embodiments, the identity of the precursor particle pn+ may be known. In either case, the identities and abundances of some or all of the various fragments of the precursor particle pn+ may be determined following fragmentation of the precursor particle in its partially or fully unfolded state.

Example 8

Yet another application of the instrument 100 illustrated in FIG. 2 is the identification of different precursor particles which have identical conformations and charge states in their folded or native states such that they cannot otherwise be distinguished from one another using conventional ion analysis techniques. In this example, the ion activation stage 17 is included in the instrument 100. In the molecule energizing stage 16, at least one structural change is induced in a complex contained in at least one of the droplets 40 generated by the droplet generator 14 as described above, the resulting structurally changed complex is then dissociated in the ion activation stage 17 and the fragment(s) are then analyzed using the ion analyzer 18 to identify the different molecules making up the complex. This application provides for identification of unknown precursor particles forming a complex via identification of at least one fragment of each particle and/or provides for abundance determinations of one or more fragments of each precursor particle.

Figure 12:
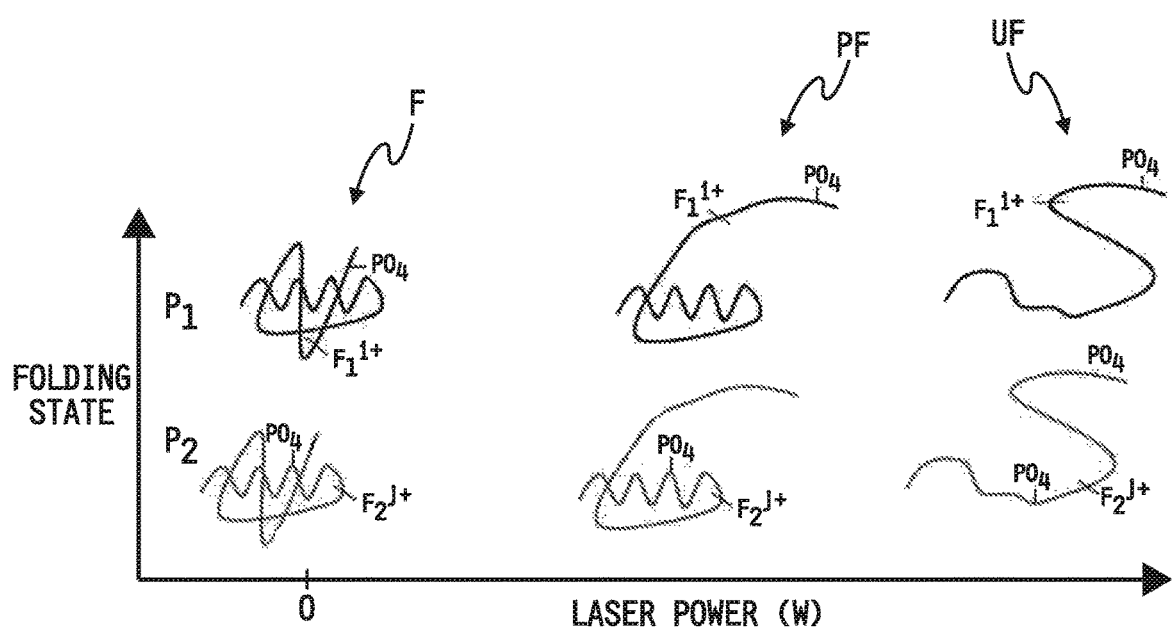
FIG. 12 is a simplified plot of folding state vs. laser power illustrating progressive unfolding of two different precursor protein particles ($P_1^{n+}$ and $P_2^{n+}$) with identical conformations from respective folded states (F), to respective partially folded (or partially unfolded) states (PF), to respective fully unfolded states (UF) with increasing laser power using the instrument of FIG. 1 or FIG. 2.
Figure 13:
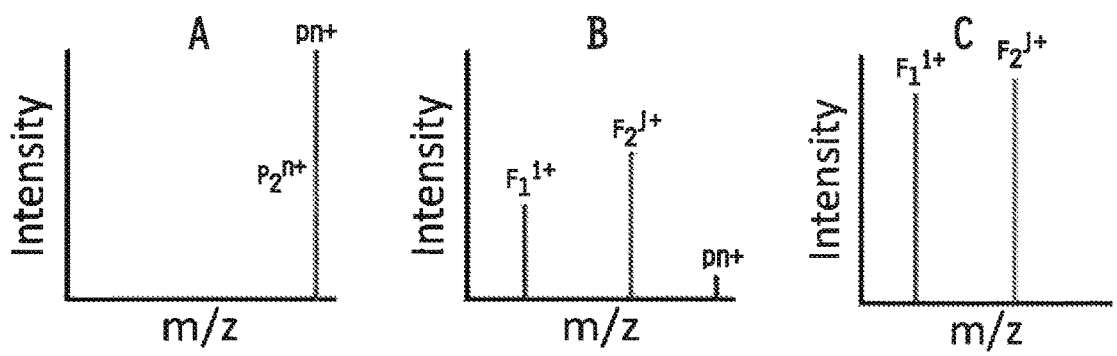
FIG. 13A is a plot of ion intensity vs. mass-to-charge ratio (m/z) illustrating intensities of the precursor particles of FIG. 12 following dissociation of the particles $P_1^{n+}$ and $P_2^{n+}$ in their respective folded states (F) using an embodiment of the instrument of FIG. 2.
FIG. 13B is a plot of ion intensity vs. mass-to-charge ratio (m/z) illustrating intensities of the precursor particles $P_1^{n+}$ and $P_2^{n+}$ of FIG. 12 and fragments thereof following dissociation of the precursor particles $P_1^{n+}$ and $P_2^{n+}$ in their respective partially unfolded states (PF) using an embodiment of the instrument of FIG. 2.
FIG. 13C is a plot of ion intensity vs. mass-to-charge ratio (m/z) illustrating intensities of the fragments of the precursor particles $P_1^{n+}$ and $P_2^{n+}$ of FIG. 12 following dissociation of the protein particles $P_1^{n+}$ and $P_2^{n+}$ in their respective unfolded states (UF) using an embodiment of the instrument of FIG. 2.
Figure 14:
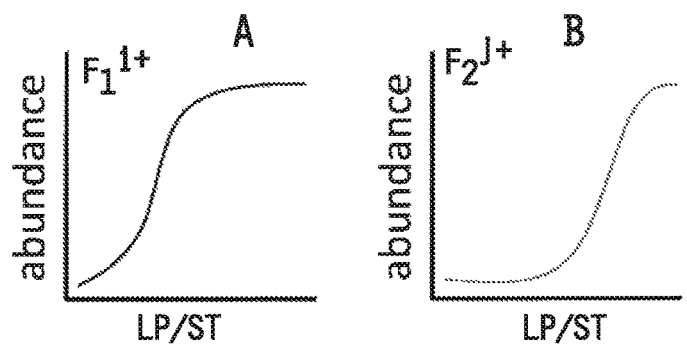
FIG. 14A is a plot of abundance vs. laser power (LP) or solution temperature (SP) illustrating abundance intensity of the protein fragment $F_1^{i+}$ of FIGS. 12 and 13A-13C as a function of increasing laser power or solution temperature.
FIG. 14B is a plot of abundance vs. laser power (LP) or solution temperature (SP) illustrating abundance intensity of the protein fragment $F_2^{j+}$ of FIGS. 12 and 13A-13C as a function of increasing laser power or solution temperature.

Referring to FIG. 12, a simplified plot is shown of molecule folding state vs. laser power for an example precursor complex including two different precursor particles $P_1$ and $P_2$. At a laser power of zero Watts, the precursor particles $P_1$ and $P_2$ are both completely folded (F). As laser power is increased, the precursor particles $P_1$ and $P_2$ begin to unfold as described above, and in the center conformation the precursor particles $P_1$ and $P_2$ are both partially folded (or unfolded) (PF). In the right-most conformation, the precursor particles $P_1$ and $P_2$ are both completely or fully unfolded (UF).

Referring to FIGS. 13A-13C, plots of intensity vs. mass-to-charge ratio (m/z) are shown, each of which represents the m/z measurement of the ion analyzer 18 following dissociation and ion analysis of the precursor complex illustrated in FIG. 12 in each respective state of unfolding. Thus, FIG. 13A represents the m/z spectrum of the precursor particles $P_1$ and $P_2$ of FIG. 9 dissociated in the activation region 17 of the instrument 100 while in their respective folded states (F), FIG. 13B represents the m/z spectrum of the precursor particles $P_1$ and $P_2$ of FIG. 9 dissociated in the activation region 17 of the instrument 100 while in their respective partially folded states (PF), and FIG. 13C represents the m/z spectrum of the precursor particles $P_1$ and $P_2$ of FIG. 12 dissociated in the active region 17 of the instrument 100 while in their respective unfolded states (UF). As depicted in FIG. 13A, dissociation of the folded precursor particles $P_1$ and $P_2$ in their folded states leaves the precursor particles $P_1$ and $P_2$ substantially intact. Moreover, because the precursor particles $P_1$ and $P_2$ have identical conformations in their respective folded states, FIG. 13A illustrates that the precursor particles $P_1$ and $P_2$ cannot be distinguished from one another using conventional ion analysis instruments and techniques since each has the same m/z value at which the intensities of the particles sum together to produce a single peak pn+.

With the precursor particles $P_1$ and $P_2$ each partially unfolded (PF) via the molecule energizing stage 16 as illustrated in FIG. 12, the composite precursor complex pn+ is substantially diminished in intensity as compared with FIG. 13A, and prominent intensity peaks of the fragments $F_1^{i+}$ and $F_2^{j+}$ of the respective precursor particles $P_1$ and $P_2$ have emerged, each at different, distinct m/z values. With the precursor particles $P_1$ and $P_2$ each fully unfolded (UF) via the molecule energizing stage 16 as illustrated in FIG. 12, the composite precursor complex pn+ is no longer detectable, and strong intensity peaks of the fragments $F_1^{i+}$ and $F_2^{j+}$ of the respective precursor particles $P_1$ and $P_2$ predominate.

Referring to FIGS. 14A and 14B, abundances of the fragments $F_1^{i+}$ and $F_2^{j+}$ respectively are plotted against laser power LP (or solution temperature ST). As with the examples illustrated in FIGS. 11A-11C, the abundance of each fragment $F_1^{i+}$ and $F_2^{j+}$ increases with increasing laser power (or solution temperature). As also shown in FIGS. 14A and 14B, the melting transitions of the various fragments $F_1^{i+}$ and $F_2^{j+}$ are mapped to respective laser power (or solution temperature) values, and may thus be correlated to respective melting temperatures as described above in the previous examples.

In some embodiments of this example, the identities of the component particles in a precursor complex may not be known, and may be identified only by one or more fragments of each following fragmentation of the precursor complex in a partially or fully unfolded state. In other embodiments, the identities of one or more of the component particles in a precursor complex may be known. In either case, the identities and abundances of some or all of the various component particles of the precursor complex may be determined following fragmentation of the various precursor particles of the complex each in its partially or fully unfolded state.

The embodiments disclosed herein are to be considered as illustrative and not restrictive in character, it being understood that only example embodiments have been shown and described and that all changes and modifications that come within the spirit of this disclosure are desired to be protected. For example, the instrument 10, 100 described herein may illustratively be used to sort, collect and/or assemble particles, e.g., specific proteins or other particles, for subsequent analysis, e.g., via electron microscopy and/or electron cryomicroscopy. In such applications, the instrument 10, 100 may thus be implemented as an efficient mechanism for preparing samples for such subsequent analysis.

What is claimed is:

1. An instrument for energizing molecules contained in a sample solution, comprising:
    a droplet generator configured to generate charged droplets of the sample solution, the droplet generator having an elongated nozzle defining an orifice at one end thereof from which the charged droplets exit the droplet generator, the nozzle defining a first longitudinal axis passing centrally through the orifice such that the charged droplets exit the nozzle orifice in a direction generally parallel with the first longitudinal axis, and
    a molecule energizing source configured to produce a molecule energizing field, the molecule energizing source positioned relative to the nozzle orifice such that the molecule energizing field extends into at least some of the exited charged droplets along a direction non-parallel with the first longitudinal axis, the molecule energizing field carrying energy which heats or cools at least one of the exited charged droplets sufficiently to induce structural changes in at least one molecule contained in the at least one of the exited charged droplets.

2. The instrument of claim 1, wherein the nozzle orifice has an orifice diameter,
    and wherein the orifice diameter defines a diameter of the exited charged droplets.

3. The instrument of claim 2, wherein the molecules contained in the sample solution have a molecule size, and wherein the orifice diameter is sized, taking into account the molecule size, to produce the exited charged droplets having a diameter sized to carry at least one of the molecules.

4. The instrument of claim 2, wherein the molecules are protein molecules,
    and wherein the orifice diameter is sized such to produce the exited charged droplets having a diameter sized to carry only a single protein molecule.

5. The instrument of claim 1, wherein the energy carried by the molecule energizing field heats the at least one of the exited charged droplets and is sufficient to cause at the at least one molecule in the at least one exited charged droplet to undergo a melting transition prior to evaporation of the at least one exited charged droplet, carrying energy which heats or cools at least one of the exited charged droplets.

6. The instrument of claim 5, wherein the energy carried by the molecule energizing field is variable so as to cause molecules in the some of the exited charged droplets to undergo at least one denaturing transition prior to the melting transition.

7. The instrument of claim 1, wherein the molecule energizing source includes at least one laser configured to produce at least one molecule energizing field to heat the at least one of the exited charged droplets, and the at least one molecule energizing field includes at least one corresponding collimated radiation field.

8. The instrument of claim 7, wherein the at least one laser is configured to produce the at least one corresponding collimated radiation field with variable radiation intensity,
    and further comprising a processor for controlling the at least one laser to produce the at least one corresponding collimated radiation field with a radiation intensity sufficient to induce structural changes in the at least one molecule contained in the at least one of the exited charged droplets.

9. The instrument of claim 1, wherein the molecule energizing source includes one of a source of heated gas configured to produce the molecule energizing field in the form of a jet or plume of heated gas, a heated capillary positioned such that the generated droplets pass longitudinally therethrough and configured to produce the molecule energizing field in the form of a thermal energy field within the heated capillary and a microwave source configured to produce the molecule energizing field in the form of a microwave radiation field.

10. The instrument of any of claim 1, further comprising:
    an ion separation instrument having an ion inlet in-line with and spaced apart from the nozzle orifice, the ion separation instrument configured to separate charged particles in time as a function of at least one molecular characteristic, and
    means for establishing an electric field between the nozzle and the ion inlet, the electric field configured to draw the charged droplets exiting the nozzle orifice in the direction generally parallel with the first longitudinal axis into the ion inlet of the ion separation instrument,
    wherein the molecule energizing source is positioned between the nozzle orifice and the ion inlet such that at least some of the charged droplets moving between the nozzle orifice and the ion inlet under the influence of the electric field pass through the molecule energizing field.

11. The instrument of claim 10, wherein the ion separation instrument is configured to separate ions as a function of ion mass-to-charge ratio.

12. The instrument of claim 10, wherein the ion separation instrument is configured to separate ions as a function of ion mobility.

13. The instrument of claim 10, wherein the ion separation instrument comprises:
- a first ion separation instrument defining the ion inlet and having a first ion outlet, the first ion separation instrument configured to separate ions between the ion inlet and the first ion outlet as a function of ion mobility, and
- a second ion separation instrument having an ion inlet coupled to the first ion outlet and a second ion outlet, the second ion separation instrument configured to separate ions between the ion inlet thereof and the second ion outlet as a function of ion charge-to-mass ratio.

14. The instrument of claim 10, further comprising at least one ion trap positioned in-line with the ion separation instrument upstream of the ion inlet or downstream of an ion outlet of the ion separation instrument, the at least one ion trap configured to selectively collect ions therein and to selectively release ions therefrom.

15. The instrument of claim 10, further comprising at least one fragmentation chamber disposed in-line with the ion separation instrument upstream of the ion inlet or downstream of an ion outlet of the ion separation instrument, the at least one fragmentation chamber configured to fragment ions resident therein.

16. The instrument of claim 12, wherein the ion separation instrument comprises an ion mobility instrument including at least one fragmentation region integral therewith and positioned between the ion inlet and an ion outlet of the ion mobility instrument, the at least one fragmentation region configured to fragment ions resident therein.

17. The instrument of claim 10, further comprising:
- an ion detector positioned at an ion outlet of the ion separation instrument, the ion detector producing ion detection signals in response to detection of ions exiting the ion outlet of the ion separation instrument, and
- a processor operatively coupled to the ion detector to receive ion detection signals produced by the ion detector, the processor configured to process the ion detection signals to produce information relating to molecules in the at least some of the charged droplets passing through the molecule energizing field.

18. The instrument of claim 17, further comprising at least one peripheral output device operatively coupled to the processor and configured to display the information relating to molecules in the at least some of the charged droplets passing through the molecule energizing field.

19. The instrument of claim 18, further comprising a memory unit operatively coupled to or integral with the processor, the processor configured to store in the memory unit at least a portion of the information relating to molecules in the at least some of the charged droplets passing through the molecule energizing field.

20. The instrument of any of claim 1, further comprising a molecular separation instrument having an inlet coupled to the sample solution and an outlet coupled to the droplet generator, the molecular separation instrument configured to separate molecules in the sample solution prior to generation of the charged droplets by the droplet generator.

21. The instrument of claim 20, wherein the molecular separation instrument comprises a liquid chromatograph including a molecule separation column configured to separate molecules in the sample solution.

22. The instrument of claim 21, wherein the molecular separation instrument further comprises a mixing chamber to mix elutes exiting the molecule separation column prior to generation of the charged droplets by the droplet generator.

23. The instrument of any of claim 1, wherein the droplet generator is an electrospray ionization unit.

24. An instrument for energizing molecules contained in a sample solution, comprising:
- a droplet generator configured to generate charged droplets of the sample solution, the droplet generator having an elongated nozzle defining an orifice at one end thereof from which the charged droplets exit the droplet generator, the nozzle defining a first longitudinal axis passing centrally through the orifice such that the charged droplets exit the nozzle orifice in a direction generally parallel with the first longitudinal axis, and
- a molecule energizing source configured to produce energy and positioned relative to the nozzle orifice such that the produced energy is applied in a direction non-parallel with the first longitudinal axis to at least one of the charged droplets exiting the droplet generator, the produced energy inducing at least one structural change in at least one molecule contained in the at least one of the charged droplets.

25. The instrument of claim 24, wherein the molecule energizing source includes at least one laser configured to produce a molecule energizing field carrying the produced energy and extending into at least some of the charged droplets along a direction non-parallel with the first longitudinal axis, the produced energy carried by the molecule energizing field heating the at least one of the charged droplets sufficiently to induce the at least one structural change in the at least one molecule contained in the at least one of the charged droplets.

26. The instrument of claim 24, wherein the molecule energizing source includes at least one thermal energy source configured to produce the energy in the form of thermal energy which extends into at least some of the charged droplets along a direction non-parallel with the first longitudinal axis and which heats or cools the at least one of the charged droplets sufficiently to induce the at least one structural change in the at least one molecule contained in the at least one of the charged droplets.

27. The instrument of claim 26, wherein the at least one thermal energy source includes a gas source configured to produce the thermal energy in the form of a heated gas jet or plume.

28. The instrument of claim 26, wherein the at least one thermal energy source comprises:
- a tube separate from the nozzle and defining a passageway through which the at least one of the charged droplets passes, and
- a heating source configured to heat the tube to produce the thermal energy within the passageway.

29. The instrument of claim 24, wherein the molecule energizing source comprises a microwave radiation source configured to produce the molecule energizing field in the form of a microwave radiation field.

30. The instrument of claim 24, wherein the produced energy induces a chemical reaction within the at least one of the charged droplets, the induced chemical reaction within the at least one of the charged droplets resulting in the at least one structural change in at least one molecule contained in the at least one of the charged droplets.

* * * * *